US011421247B2

(12) United States Patent
Tomonaga et al.

(10) Patent No.: US 11,421,247 B2
(45) Date of Patent: Aug. 23, 2022

(54) BORNA VIRAL VECTOR AND USE THEREOF

(71) Applicant: Kyoto University, Kyoto (JP)

(72) Inventors: Keizo Tomonaga, Kyoto (JP); Akiko Makino, Kyoto (JP)

(73) Assignee: Kyoto University, Kyoto (JP)

( * ) Notice: Subject to any disclaimer, the term of this patent is extended or adjusted under 35 U.S.C. 154(b) by 476 days.

(21) Appl. No.: 16/493,232

(22) PCT Filed: Mar. 6, 2018

(86) PCT No.: PCT/JP2018/008652
§ 371 (c)(1),
(2) Date: Sep. 11, 2019

(87) PCT Pub. No.: WO2018/168586
PCT Pub. Date: Sep. 20, 2018

(65) Prior Publication Data
US 2020/0131531 A1 Apr. 30, 2020

(30) Foreign Application Priority Data
Mar. 14, 2017 (JP) .............................. JP2017-049247

(51) Int. Cl.
| C12N 15/86 | (2006.01) |
| A61K 39/12 | (2006.01) |
| C07H 21/04 | (2006.01) |
| C07K 14/005 | (2006.01) |
| C07K 14/115 | (2006.01) |
| A61K 35/76 | (2015.01) |
| C12N 7/00 | (2006.01) |
| C12N 9/12 | (2006.01) |

(52) U.S. Cl.
CPC .............. *C12N 15/86* (2013.01); *A61K 35/76* (2013.01); *C12N 7/00* (2013.01); *C12N 9/127* (2013.01); *C12N 2760/00041* (2013.01); *C12N 2799/02* (2013.01); *C12N 2800/50* (2013.01)

(58) Field of Classification Search
CPC ............ A61K 2300/00; A61K 38/1774; A61K 38/208; A61P 35/00; C12N 15/86
See application file for complete search history.

(56) References Cited

U.S. PATENT DOCUMENTS

2012/0151614 A1   6/2012   Tomonaga et al.

FOREIGN PATENT DOCUMENTS

| EP | 2415866 A1 | 2/2012 |
| JP | 2010-22338 A | 2/2010 |
| JP | 2017-00015 A | 1/2017 |
| WO | WO 2010/006296 A2 | 1/2010 |
| WO | WO2010/113647 | * 10/2010 |
| WO | WO 2010/113647 A1 | 10/2010 |

OTHER PUBLICATIONS

Daito, Takuji et al., "A Novel Borna Disease Virus Vector System That Stably Expresses Foreign Proteins from an Intercistronic Noncoding Region" Journal of Virology, Dec. 2011, pp. 12170-12178, vol. 85, No. 23.
Ikeda, Y. et al., "A novel intranuclear RNA vector system for long-term stem cell modification" Gene Therapy, 2016, pp. 256-262, vol. 23.
Sakai, Madoka et al., "603 . Development of Transmission-Deficient Borna Disease Virus Vector with Enhanced Transduction Efficiency in Primary and Stem Cells" Molecular Therapy, May 2018, pp. 279-280, vol. 26, No. 5S1.
Supplementary European Search Report for EP 18767188 dated Aug. 13, 2020.
Fujino, Kan et al., "Generation of a non-transmissive Borna disease virus vector lacking both matrix and glycoprotein genes" Microbiol Immunol, 2017, pp. 380-386, vol. 61.
Schneider, Urs et al., "A Borna Disease Virus Vector for Expression of Foreign Genes in Neurons of Rodents" Journal of Virology, Jul. 2007, pp. 7293-7296, vol. 81, No. 13.
Tomonaga, Keizo "Borna Byo Uirusu Kansen to Chusushinkei Shikkan", Saishin Igaku, (offprint from the Feb. 2005 issue), pp. 79-85, vol. 60, No. 2.

(Continued)

*Primary Examiner* — Barry A Chestnut
(74) *Attorney, Agent, or Firm* — Knobbe Martens Olson & Bear LLP

(57) ABSTRACT

Disclosed is a viral vector comprising (a) a cDNA of a recombinant viral RNA having a sequence of a Borna disease viral genome comprising a disrupted G gene of the Borna disease viral genome and an inserted G gene of an avian bornaviral genome, wherein the cDNA of the recombinant viral RNA has at least an N gene, an X gene, a P gene and an L gene of the Borna disease viral genome in the same order as in the Borna disease viral genome and has an inserted foreign gene; (b) DNAs encoding ribozymes; and (c) a promoter sequence, wherein (b) the DNAs encoding ribozymes are located upstream and downstream of (a) the cDNA of the recombinant viral RNA, and (a) the cDNA of the recombinant viral RNA and (b) the DNAs encoding ribozymes are located downstream of (c) the promoter sequence. The present invention can be used as a gene introduction technique that does not affect a host chromosome and can be suitable for the application in various fields, such as the treatment and prevention of brain and neurological diseases, visualization techniques of nerve cells in the field of neuroscience, etc.

12 Claims, 7 Drawing Sheets
Specification includes a Sequence Listing.

(56) References Cited

OTHER PUBLICATIONS

Protein, Nucleic Acid and Enzyme, 2017, pp. 1168-1174, vol. 52, No. 10.
International Search Report for PCT/JP2018/008652 dated May 29, 2018.
International Preliminary Report on Patentability for PCT/JP2018/008652 dated Sep. 17, 2019.

* cited by examiner

Fig. 8

SEQUENCE LISTING

<160> NUMBER OF SEQ ID NOS: 19

<210> SEQ ID NO 1
<211> LENGTH: 8908
<212> TYPE: DNA
<213> ORGANISM: Borna disease virus

<400> SEQUENCE: 1

```
gttgcgttaa caacaaacca atcattatcc ttctaacaaa atgaacacac gcaatgccac      60
ccaagagacg cctggttgat gacgccgatg ccatggagga ccaagattta tatgaacccc     120
cagcgagcct ccccaagctc cccggaaaat tcctacaata caccgttggg gggtctgacc     180
cgcatccggg tatagggcat gagaaggata tcaggcagaa cgcagtggca ttgttagacc     240
agtcacggcg cgatatgttt catacagtaa cgcccagcct tgtgtttcta tgtttgctaa     300
tcccaggact gcacgctgcg tttgttcacg gaggggtgcc tcgtgaatct tacctgtcga     360
cgcctgttac gcgtggggaa cagactgtcg ttaagactgc aaagttttac ggggaaaaga     420
caacacagcg tgatctcacc gagctggaga tctcctctat attcagccat tgttgctcat     480
tactaattgg ggttgtgata ggatcgtcat ctaagattaa agcaggagcc gagcagatca     540
agaaaaggtt taaaactatg atggcagcct taaaccggcc atcccatggt gagactgcta     600
cactacttca gatgtttaat ccacatgagg ctatagattg gattaacggc cagccctggg     660
```

```
taggctcctt tgtgttgtct ctactaacta cagactttga gtccccaggt aaagaattca    720
tggatcagat taaacttgtc gcaagttatg cgcagatgac tacgtacact actataaagg    780
agtacctcgc agaatgtatg gatgctaccc ttacaatccc tgtagttgca tatgagattc    840
gtgactttt agaagtttca gcaaagctta agaggaaca tgctgacctg tttccgttcc      900
tgggggctat tcggcacccc gacgctatca agcttgcgcc acggagcttt cccaatctgg    960
cttctgcagc gttttactgg agtaagaagg agaatcccac aatggcgggc taccgggcct   1020
ccaccatcca gccgggcgcg agtgtcaagg agacccagct tgcccggtat aggcgccgcg   1080
agatatctcg cggggaagac ggggcagagc tctcaggtga gatctctgcc ataatgagaa   1140
tgataggtgt gactggtcta aactagaaaa caatgaacaa accaataaaa aaccaaatgc   1200
ggcaaacccc ccgcgacctg tgatgagttc cgacctccgg ctgacattgc ttgaattagt   1260
caggaggctc aatggcaacg ggaccatcga gtctggtcga ctccctggag gacgaagaag   1320
atccccagac actacgacgg gaacgatcgg ggtcaccaag accacggaag atcccaagga   1380
atgcattgac ccaaccggta gaccagctcc tgaaggacct caggaagaac ccctccatga   1440
tctcagaccc agaccagcga accggaaggg agcagctatc gaatgatgag cttatcaaga   1500
agctagtgac ggagctggcc gagaaatagca tgatcgaggc tgaggaggtg cggggcactc   1560
ttggggacat ctcggctcgc atcgaggcag ggtttgagtc cctgtccgcc ctccaagtgg   1620
aaaccatcca gacagctcag cggtgcgacc actccgatag catcagaatc cttggcgaga   1680
acatcaagat actggatcgc tccatgaaga caatgatgga gacaatgaag ctcatgatgg   1740
agaaggtgga cctcctctac gcatcaaccg ccgttgggac ctctgcaccc atgttgccct   1800
cccatcctgc acctccgcgc atttatcccc agctcccaag tgccccgaca gcggatgagt   1860
gggacatcat accataaaaa aatcgaatca ccatgaattc aaagcattcc tatgtggagc   1920
tcaagggcaa ggtaatcgtc cctggatggc ccacactgat gcttgagata gactttgtag   1980
gagggacttc acggaaccag ttccttaaca tcccatttct ttcagtgaaa gagcctctgc   2040
agcttccacg cgagaagaag ttgaccgact acttcaccat tgacgtagag ccagcaggtc   2100
attccctggt caacatatac ttccagattg acgacttctt gctcctaaca ctcaactcac   2160
tgtccgtata caaggacccg attaggaaat acatgttcct acgcctcaac aaggaacaga   2220
gcaagcacgc aattaatgca gctttcaatg tcttctctta tcggcttcgg aacattggtg   2280
ttggccctct cggcccagac attcgatctt cagggcctta gttgcaatac tgactccact   2340
cctggattaa tcgatctgga gataaggcga ctttgccaca ccccaacgga aaatgtcatt   2400
tcatgcgagg ttagttatct taaccacacg actattagcc tcccggcagt ccacacgtca   2460
tgcctcaagt accactgcaa aacctattgg ggattctttg gtagctacag cgctgaccga   2520
atcatcaatc ggtacactgg tactgttaag ggttgtttaa acaactcagc gccagaggat   2580
cccttcgagt gcaactggtt ctactgctgc tcggcgatta acagagagat ctgccgatgc   2640
tctattacaa atgtcacggt ggctgtacag acattccacc cgttcatgta ctgcagtttc   2700
gcggactgta gtactgtgag tcagcaggag ctagagagtg gcaaggcaat gctgagcgat   2760
ggcagtacct taacttatac cccgtatatc ttacaatcag aagtcgtgaa caaaacccctt  2820
aatgggacta tactctgcaa ctcatcctcc aagatagttt ccttcgatga atttaggcgt   2880
tcatactccc tagcgaatgg tagttaccag agctcatcaa tcaatgtgac gtgtgtaaac   2940
tacacgtcgt cctgccggtc caagttgaga aggcggcgta gggatactca acagattgag   3000
tacctagttc acaagcttag gcctacactg aaagatgcgt gggaggactg tgagatcctc   3060
```

```
cagtctctgc tcctagggat gtttggtact gggattgcaa gtgcttcgca attcttgagg    3120
ggctggctca accaccctga tatcatcggg tatatagtta atggagttgg ggtagtctgg    3180
caatgccatc gtgttaatgt cacgttcatg gcgtggaatg agtccacata ttaccctcca    3240
gtagattaca atggacggaa gtactttctg aatgatgagg ggaggctaca aacaaacacc    3300
cccgaggcaa ggccagggct taagcgggtc atgtggttcg gcaggtactt cctagggaca    3360
gtagggtctg gggtgaaacc gaggaggatt cggtacaata agacctcaca tgattaccat    3420
ctagaggagt ttgaggcaag tctcaacatg accccccaga ccagtatcgc ctcgggtcat    3480
gagacagacc ccataaatca tgcctacgga acgcaggctg acctccttcc atacaccagg    3540
tctagtaata taacgtctac agatacaggc tcaggctggg tgcacatcgg cctaccctca    3600
tttgctttcc tcaatcctct cggtggctt agggacctac ttgcgtgggc ggcctggttg    3660
ggtggggttc tatacttaat aagtctttgt gtttccttac cagcctcctt cgcgaggagg    3720
agacgcctcg gccggtggca ggaataaacc gtaccgacca aactcttaaa aaccctcttc    3780
tcgggacaga ggtctctttc tgccttaaat cgagttcact cccccatcac gtacgagcat    3840
tgggccagat taaagcaaag aacctggcat cctgtgacta ttacttgcta ttccgccaag    3900
ttgtattgcc ccctgaagta tatcccattg gtgtcttaat aagagctgcg gaggccatac    3960
taacagttat agtatcagct tggaagctgg atcacatgac aaagacccta tactcctctg    4020
tgagatatgc actcaccaat ccccgggtcc gggcccaact tgagctccac attgcctacc    4080
agcgcatagt gggtcaggtc tcgtatagcc gggaagcaga tatagggcca aaaaggcttg    4140
ggaatatgtc attgcaattc atccaatccc tcgttattgc caccatagac acaacgagct    4200
gcctaatgac ctacaaccac tttcttgctg cagcagacac agccaagagc agatgccacc    4260
tcctaatcgc ctcagtggtc caaggagccc tttgggagca agggtcattt cttgatcata    4320
taatcaacat gatcgacaca attgactcaa tcaacctccc ccatgatgat tacttcacaa    4380
ttattaagtc tatctctccc tactcccaag ggcttgttat ggggaggcac aatgtgtcag    4440
tctcctctga ttttgcgtcc gtatttacta ttcctgaatc atgcccacaa ctagacagct    4500
tactaaaaaa actgcttcaa cttgaccctg ttctcctcct catggtctct tcggtgcaga    4560
agtcatggta cttccctgag atccgaatgg ttgacgggtc acgggagcag ctccacaaga    4620
tgcgtgtcga gctggagacg ccccaagccc tgctgtcata cggccatacc ctcctgtcaa    4680
tatttcgagc agagtttatc aaaggctatg tctcaaagaa tgcgaagtgg ccgcctgtac    4740
acctgctccc aggctgtgac aaatccataa agaatgcgag agagctgggc cgctggagcc    4800
cggtgtttga ccgacgatgg cagctcttcg cgaaggttgt cattctaaga attgctgacc    4860
tagatatgga tcccgacttc aacgatattg ttagcgacaa ggcgataatc agctcaagaa    4920
gggactgggt atttgagtac aatgcagcag ccttttggaa gaaatacagt gagcggttgg    4980
agaggccccc tgccagatcg ggaccatcac ggccttgtgaa tgctctgatc gatgacgct    5040 tagataatat cccagccctg ctagagccat tttacagggg agcggttgag tttgaggatc    5100
ggctgactgt gctcgtgcct aaggagaagg agttgaaggt aaagggaagg ttcttctcga    5160
agcaaacatt ggcaatcagg atatatcagg ttgttgctga agctgcactt aagaacgagg    5220
ttatgccata cttaaaaaca cattcaatga ccatgagctc aacggcccta acccatcttc    5280
ttaaccggct atcacatact atcactaagg gtgactcctt tgttattaac ttagattata    5340
gctcctggtg caacggtttc cgaccagaac tacaagcccc actctgtcgt cagttggatc    5400
```

```
agatgttcaa ttgcgggtac ttcttcagga ctgggtgcac actgccatgc tttaccacgt   5460
ttattattca ggacagattc aacccgccct attccttccg tggtgagccc gttgaagacg   5520
gtgtcacatg cgcggttggg actaagacaa tgggagaggg tatgaggcag aaactatgga   5580
caattcttac gagctgctgg gagataattg ctcttcggga aattaacgtg acgtttaata   5640
tactaggcca gggtgataat cagacaatca ttgtacataa atctgcaagc caaaataatc   5700
agctattagc ggagcgagca ttgggagctt tgtacaagca tgctagatta gctggccata   5760
accttaaggt agaagaatgt tgggtgtcag attgtctgta tgagtatgga aagaagctct   5820
tcttccgtgg tgtacctgtc ccaggctgtt gaagcagct ctcgcgggtg acggactcca    5880
ctggggagtt attcccaaac ctatactcaa agttagcctg cttaacatca tcatgcttaa   5940
gcgcagcgat ggcagacaca tccccatggg tggcactcgc gacaggtgtc tgtctgtatc   6000
ttatcgagtt gtatgttgag ctgcctccgg caatcatgca ggacgagtcg ctgttaacga   6060
ccctctgtct cgtaggtcca tccattggtg ggcttccaac tcctgcaacc ctgcccagtg   6120 tcttttcag aggaatgtcc gacccattgc cctttcagct agcactcttg cagaccctca    6180
ttaaaacgac aggggtgact tgtagcttgg tgaatcgtgt ggttaagtta cggatagcac   6240
cctatccaga ctggctctcc ctagtgactg acccgacttc actcaacatt gctcaggtgt   6300
accggccaga acgtcaaatc aggaggtgga ttgaggaggc aatagcaaca agctcacact   6360
cgtcacgcat agcaactttt ttccagcagg ccctcacgga gatggcccag ctgcttgcga   6420
gggacctctc aacaatgatg cctcttcggc cccgggatat gtcggcctta ttcgcattat   6480
caaatgtcgc atatggtcta agcattatag atctatttca aaagtcctct accgttgtct   6540
ctgcaagtca agctgtccat atcgaagatg ttgccctaga gagtgtaagg tataaggaat   6600
ctatcattca gggtctgtta gacactactg aggggtacaa catgcaacct tatttggaag   6660
gttgcactta ccttgcagcc aagcagctac ggaggttgac gtggggtcga gacctagttg   6720
gagttacaat gccgtttgtt gccgagcaat tccatcccca tagttctgtc ggtgcaaaag   6780
cagaactcta cctcgatgct atcatatact gcccacaaga gacgttgcgg tcacaccatc   6840
tgactaccag gggggaccag ccgctttacc ttggatctaa tacggctgtc acggttcagc   6900
gaggtgagat cacaggccta acaaagtcaa gggctgcaaa tctagtcaag gacactctcg   6960
ttctccacca gtggtacaag gtccgtaagg ttaccgatcc acacttgaac actctcatgg   7020
cgcgcttctt gcttgagaag ggatacacat ctgacgctcg gcctagcatt cagggtggga   7080
ccctcacaca tcgtctccca tcccgtggag actcacgcca agggctcact gggtatgtga   7140
atatactcag cacgtggctc cggttctcaa gtgattatct tcactctttc tcgaaatcat   7200
cagatgacta cacaatccac ttccagcatg tattcacata cggttgcctc tatgctgatt   7260
cggtgattag atcgggcggt gttatttcca ctccttacct tttgagtgca agttgtaaaa   7320
catgctttga gaagatagac tcagaggagg tcgtcctggc atgcgaacct caatatgggg   7380
gtgctgagtg gctgatatca aagccagtta ctgtccctga gcagataatt gacgctgaag   7440
tcgagtttga cccctgtgtg agtgcgagtt attgtctcgg gattctcatt ggcaagtcat   7500
tcttggttga cataagggca agtgggcatg atattatgga gcagcggaca tgggctaact   7560
tggagaggtt ttctgtgtcg gacatgcaga aacttccatg gagtattgta attcggtctc   7620
tctggagatt ccttattggc gcacgactcc tccagtttga gaaggctggc cttattagga   7680
tgctgtatgc tgcaacaggt ccaacccttta gcttcctaat gaaagtcttt caagactcag   7740
ccctacttat ggactgcgca cctcttgatc ggctgtaccc taggatcaac tttcatagtc   7800
```

```
ggggagacct cgtcgccaag ctcgtttat taccttcat caacccgggt atagtggaga    7860
ttgaagtgtc tagaattaat agcaagtatc atgcagtatc ggaggctaat atggatctgt   7920
acatcgctgc tgcaaaatct gtgggcgtaa agcccacaca gtttgttgag gaaacaaacg   7980
actttacggc ccgcggccac caccatggtt gttattccct ttcttggtct aagtcacgca   8040
atcaatcaca ggtcctaaag atggtagtgc ggaagctgaa gctatgtgtc ctgtatatat   8100
accccacagt cgatcccgcc gttgctctcg acctgtgcca cctgccagca ctaactataa   8160
tcctagtgct cggcggtgac ccagcgtact acgagcgatt acttgagatg gacctatgcg   8220
gggctgtgtc aagtcgcgtt gatatccccc attccctagc tgccagaacg cacagggggg   8280
tcacaatagg cccagacgct ggtccaggtg tgattagact tgacaagtta gagtcggttt   8340
gttacgccca ccctgtttg gaggagctag agtttaatgc gtacctagac tctgagttag   8400
ttgatattag tgatatgtgc tgcctcccc tagcgacacc ctgtaaggcc ctattcaggc   8460
cagtgtatcg gagcttacag tcgttcaggt tagccttaat ggacaactat agttttgtaa   8520
tggacctcat tacgatccgg ggggtggaca tcaggcctca ccttgaggag tttgatgaac   8580
tgcttgtggt ggggcagcat atcctcggtc agcccgtcct agtggaggtt gtttactacg   8640
ttggagttgt tgggaagcgt cctgtgttag cgaggcatcc ctggtcagca gatcttaagc   8700
gaatcactgt aggggggcga gcgccctgcc cttctgctgc tggactgcgt gatgaggatt   8760
gtcgggggtc tctgctggtt gggcttcccg ctggattgac gcagttgttg gtggttgatt   8820
gaggttgagc catctactgc cctattctta aaaaaccata cgtcagtggt gcagtgcttg   8880
ggtttggttg ttgctttgtt gtagcgct                                     8908

<210> SEQ ID NO 2
<211> LENGTH: 72
<212> TYPE: RNA
<213> ORGANISM: Artificial
<220> FEATURE:
<223> OTHER INFORMATION: Synthetic oligonucleotide

<400> SEQUENCE: 2
uuguagccgu cugaugaguc cgugaggacg aaacuauagg aaaggaauuc cuauagucag    60
cgcuacaaca aa                                                       72

<210> SEQ ID NO 3
<211> LENGTH: 72
<212> TYPE: RNA
<213> ORGANISM: hepatitis delta virus

<400> SEQUENCE: 3
ggccggcaug gucccagccu ccucgcuggc gccggcuggg caacaccauu gcacuccggu    60
ggcgaauggg ac                                                       72

<210> SEQ ID NO 4
<211> LENGTH: 113
<212> TYPE: DNA
<213> ORGANISM: SV40 virus

<400> SEQUENCE: 4 aagcttttg caaaagccta ggcctccaaa aaagcctcct cactacttct ggaatagctc    60
agaggccgag gcggcctcgg cctctgcata ataaaaaaa attagtcagc cat           113

<210> SEQ ID NO 5
```

```
<211> LENGTH: 30
<212> TYPE: DNA
<213> ORGANISM: Artificial
<220> FEATURE:
<223> OTHER INFORMATION: Oligonucleotide for primer

<400> SEQUENCE: 5
ggaatgcatt gacccaaccg gtagaccagc                                    30

<210> SEQ ID NO 6
<211> LENGTH: 34
<212> TYPE: DNA
<213> ORGANISM: Artificial
<220> FEATURE:
<223> OTHER INFORMATION: Oligonucleotide for primer

<400> SEQUENCE: 6
aacatgtatt tcctaatcgg gtccttgtat acgg                               34

<210> SEQ ID NO 7
<211> LENGTH: 41
<212> TYPE: DNA
<213> ORGANISM: Artificial
<220> FEATURE:
<223> OTHER INFORMATION: Oligonucleotide for primer

<400> SEQUENCE: 7
ttcgaaggtt ggttaattaa ccataaaaaa atcgaatcac c                       41

<210> SEQ ID NO 8
<211> LENGTH: 41
<212> TYPE: DNA
<213> ORGANISM: Artificial
<220> FEATURE:
<223> OTHER INFORMATION: Oligonucleotide for primer

<400> SEQUENCE: 8
ttaattaacc aaccttcgaa ggtgattcga ttttttatg g                        41

<210> SEQ ID NO 9
<211> LENGTH: 16
<212> TYPE: DNA
<213> ORGANISM: Borna disease virus

<400> SEQUENCE: 9
taaaaaaatc gaatca                                                   16

<210> SEQ ID NO 10
<211> LENGTH: 34
<212> TYPE: DNA
<213> ORGANISM: Artificial
<220> FEATURE:
<223> OTHER INFORMATION: Oligonucleotide for primer

<400> SEQUENCE: 10
ccgtatacaa ggacccgatt aggaaataca tgtt                               34

<210> SEQ ID NO 11
<211> LENGTH: 32
<212> TYPE: DNA
<213> ORGANISM: Artificial
<220> FEATURE:
<223> OTHER INFORMATION: Oligonucleotide for primer

<400> SEQUENCE: 11
aagagaagac gttgaaagct gcgttaattg cg                                 32
```

<210> SEQ ID NO 12
<211> LENGTH: 32
<212> TYPE: DNA
<213> ORGANISM: Artificial
<220> FEATURE:
<223> OTHER INFORMATION: Oligonucleotide for primer

<400> SEQUENCE: 12
cgcaattaac gcagctttca acgtcttctc tt                                32

<210> SEQ ID NO 13
<211> LENGTH: 29
<212> TYPE: DNA
<213> ORGANISM: Artificial
<220> FEATURE:
<223> OTHER INFORMATION: Oligonucleotide for primer

<400> SEQUENCE: 13
gggtctgcaa gagtgctagc tgaaagggc                                    29

<210> SEQ ID NO 14
<211> LENGTH: 33
<212> TYPE: DNA
<213> ORGANISM: Artificial
<220> FEATURE:
<223> OTHER INFORMATION: Oligonucleotide for primer

<400> SEQUENCE: 14
gcgaaggagg ctcgcatgaa atgacatttt ccg                               33

<210> SEQ ID NO 15
<211> LENGTH: 35
<212> TYPE: DNA
<213> ORGANISM: Artificial
<220> FEATURE:
<223> OTHER INFORMATION: Oligonucleotide for primer

<400> SEQUENCE: 15
tcatttcatg cgagcctcct tcgcgaggag gagac                             35

<210> SEQ ID NO 16
<211> LENGTH: 16
<212> TYPE: DNA
<213> ORGANISM: Artificial
<220> FEATURE:
<223> OTHER INFORMATION: Inserted oligonucleotide

<400> SEQUENCE: 16
taaaaaaatc gaatca                                                  16

<210> SEQ ID NO 17
<211> LENGTH: 8
<212> TYPE: DNA
<213> ORGANISM: Artificial
<220> FEATURE:
<223> OTHER INFORMATION: Inserted oligonucleotide

<400> SEQUENCE: 17 taaaaaaa                                                            8

<210> SEQ ID NO 18
<211> LENGTH: 36
<212> TYPE: DNA
<213> ORGANISM: Artificial
<220> FEATURE:

```
<223> OTHER INFORMATION: Oligonucleotide for primer

<400> SEQUENCE: 18
aaaggcgcgc catgctgcat tcaacgtatt ctcgtt                                36

<210> SEQ ID NO 19
<211> LENGTH: 32
<212> TYPE: DNA
<213> ORGANISM: Artificial
<220> FEATURE:
<223> OTHER INFORMATION: Oligonucleotide for primer

<400> SEQUENCE: 19
aaagcgatcg cttattccga ccaccttccg ag                                    32
```

BORNA VIRAL VECTOR AND USE THEREOF

CROSS REFERENCE TO RELATED APPLICATIONS

This application is a U.S. National Phase Application of PCT International Application Number PCT/JP2018/008652, filed on Mar. 6, 2018, designating the United States of America and published in the Japanese language, which is an International Application of and claims the benefit of priority to Japanese Patent Application No. 2017-049247, filed on Mar. 14, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT009-003APC.txt, the date of creation of the ASCII text file is Aug. 21, 2019, and the size of the ASCII text file is 15 KB.

TECHNICAL FIELD

The present invention relates to a viral vector and a recombinant virus for introducing a foreign gene into a cell and to use of the viral vector and the recombinant virus.

BACKGROUND ART

Use of a viral vector is known as a technique for delivering a foreign gene into living bodies or cells. Until now, various vectors have been developed utilizing a retrovirus, a lentivirus, an adenovirus, an adeno-associated virus, and Sendai virus.

These conventional viral vectors, however, have the following disadvantages. For example, in cases where the vector is a DNA virus, the viral gene is integrated into a host chromosome, thereby exhibiting pathogenicity for the host (for example, humans). Some of the conventional viral vectors have a narrow host range for infection and thus can only be applied to a particular organism. In addition, the gene introduction efficiency of the conventional viral vectors is poor because the efficiency varies with the insertion site for a foreign gene into the viral genome. Further, the stability and persistency of the conventional viral vectors are poor due to elimination of the introduced virus by the immune response in a living body, mutation of the viral gene, and/or changes in the promoter efficiency.

In gene therapy or other therapies, a gene introduction technique capable of introducing a gene into only cells of interest has been desired. In particular, since gene therapy is considered to be effective for treating neurological diseases, the development of a viral vector capable of preferentially introducing a gene into nerve cells and having high safety, high stability, high persistency, and high efficiency of gene introduction has been desired.

Borna disease virus (BDV) is a neurotropic virus belonging to the order Mononegavirales and having a single non-segmented minus-strand RNA as a genome. Currently identified members of the genus Bornavirus of the family Bornaviridae include Borna disease virus (BDV), which infects mammals, and Avian Bornavirus (ABV), which infects birds.

BDV replicates itself in the cell nucleus, but its infection is non-cytotoxic and prolonged over a long period of time, and its host range is very wide (Non Patent Literature 1 and 2, etc.).

A BDV-meditated technique for introducing a foreign gene into cells has been reported in Non Patent Literature 3. In this literature, an expression cassette encoding a green fluorescent protein (GFP) is inserted into the untranslated region at the 5' end of the BDV genome, and this recombinant virus is used with a high-activity polymerase to infect rats to express the GFP gene in the nerve cells of the rats.

Patent Literature 1 discloses a viral vector comprising (a) a cDNA encoding a recombinant Borna disease virus genome containing an inserted foreign gene in the open reading frame of the G gene, (b) cDNAs encoding ribozymes, and (c) a promoter sequence, wherein (b) the cDNAs encoding ribozymes are located upstream and downstream of (a) the cDNA encoding the recombinant Borna disease virus genome, and (a) the cDNA encoding the recombinant Borna disease virus genome and (b) the cDNAs encoding ribozymes are located downstream of (c) the promoter sequence.

Patent Literature 2 discloses a viral vector comprising (a) a cDNA of a recombinant viral RNA having at least an N gene, an X gene, a P gene and an L gene of a Borna disease viral genome in the same order as in the Borna disease viral genome and having an inserted foreign gene in the untranslated region immediately downstream of the open reading frame of the P gene; (b) DNAs encoding ribozymes; and (c) a promoter sequence, wherein (b) the DNAs encoding ribozymes are located upstream and downstream of (a) the cDNA of the recombinant viral RNA, and (a) the cDNA of the recombinant viral RNA and (b) the DNAs encoding ribozymes are located downstream of (c) the promoter sequence.

CITATION LIST

Patent Literature

Patent Literature 1: JP 2010-22338 A
Patent Literature 2: WO 2010/113647

Non Patent Literature

Non Patent Literature 1: Protein, Nucleic Acid and Enzyme, Vol. 52, No. 10, 1168-1174 (2007).
Non Patent Literature 2: Keizo Tomonaga, Borna Byo Uirusu Kansen to Chusushinkei Shikkan, Saishin Igaku, Vol. 60, No. 2 (offprint from the February, 2005 issue), 79-85.
Non Patent Literature 3: U. Schneider et al., Journal of Virology (2007), 7293-7296.

SUMMARY OF INVENTION

Technical Problem

The above techniques using BDV may be capable of preferentially inserting a foreign gene into central nervous system cells. However, in the above techniques using BDV, the efficiency of recovery of a recombinant virus is low and the efficiency of gene introduction still remains low, and thus these techniques require further improvement to enhance the efficiency of gene introduction. Therefore there is a need for an improved viral vector having high replicative efficiency of a recombinant virus, a wide host range for infection, high safety, high efficiency of introduction of a foreign gene, high stability and high persistency, and a capability of preferentially introducing a foreign gene into the central nervous system.

An object of the present invention is to provide a viral vector having a wide host range for infection, high efficiency of introduction of a foreign gene, safety due to no integration of the viral genome into a host chromosome, high intracellular stability and persistency due to non-cytotoxic expression of a foreign gene in the cell nucleus, a capability of preferentially introducing a foreign gene into cells of interest (for example, central nervous system cells such as cranial nerve cells, or the like), and a capability of efficiently producing a low pathogenic (highly safe) recombinant virus due to transmissibility only to cells of interest. Another object of the present invention is to provide the recombinant virus, a method for introducing a foreign gene using the recombinant virus, a foreign gene introducing agent, etc.

Solution to Problem

In order to solve the above problems, the inventors conducted extensive research on the insertion of a foreign gene into a BDV genome (RNA viral genome). The inventors found that, when a foreign gene is inserted into a BDV genome together with a G gene having a different genotype from that of the G gene of the BDV genome, i.e., when a vector is prepared by introducing a foreign gene together with the G gene of an avian Bornavirus (ABV) into the BDV genome, the resulting recombinant virus has high productivity and high recovery rate (the recombinant virus produced from the vector has high replicative efficiency), and in turn the foreign gene is efficiently expressed in cells. That is, the inventors found that a foreign gene is very efficiently introduced into cells in this manner.

In conventional recombinant BDV vectors, a foreign gene is inserted into the G gene region (Patent Literature 1) or the 5' end region of the foreign genome (Non Patent Literature 3) for expression of the foreign gene. However, the vector in which a foreign gene is inserted in the G gene region has low productivity of a recombinant virus, and the infection of cells with the recombinant virus produced from the vector is transitory and thus the virus cannot express the foreign gene persistently. The recombinant BDV vector in which a foreign gene is inserted in the 5' end region of the genome has low efficiency of introduction of the foreign gene. Another recombinant BDV vector has been proposed, in which a foreign gene is inserted in the untranslated region between the open reading frame of the P gene and the open reading frame of the M gene (Patent Literature 2). The vector is, however, not suitable for practical use due to problems of low productivity of a recombinant virus and only a few amount of the recombinant virus that can be recovered. The inventors focused on the sequence of a BDV genome, and found that, when the original G gene is disrupted and then a foreign gene is inserted together with another G gene having a different genotype from that of the original G gene, the resulting BDV vector has higher productivity and higher recovery efficiency of a virus as compared with conventional recombinant BDV vectors, and the recombinant virus produced from the resulting vector highly efficiently infects central nervous system cells, and the infected cells express the gene of interest for a long period of time. Based on these findings, the inventors contemplated that the recombinant BDV vector can be used to efficiently introduce various foreign genes into cells of interest.

The BDV genome encodes at least six proteins: a nucleoprotein (N protein), the X protein, a phosphoprotein (P protein), a matrix protein (M protein), a surface glycoprotein (G protein), and an RNA-dependent RNA polymerase (L protein). FIG. 1 is a schematic view of the structure of a BDV genome. In FIG. 1, N, X, P, M, G, and L schematically represent the ORFs of the genes. The BDV genome has, from the 3' end, the N gene, the X gene, the P gene, the M gene, the G gene, and the L gene in this order as shown in FIG. 1. The viral RNAs encoding the G protein, the M protein, the N protein, the P protein, and the L protein are herein referred to as the G gene, the M gene, the N gene, the P gene, and the L gene, respectively. For example, "the cDNA of the G gene" means a cDNA encoding the G gene.

That is, the present invention relates to the following (1) to (15).

(1) A viral vector comprising a cDNA of a recombinant viral RNA having a sequence of a Borna disease viral genome comprising a disrupted G gene of the Borna disease viral genome and an inserted G gene of an avian bornaviral genome.

(2) The viral vector according to the above (1), which comprises:

(a) the cDNA of a recombinant viral RNA having a sequence of a Borna disease viral genome comprising a disrupted G gene of the Borna disease viral genome and an inserted G gene of an avian bornaviral genome, wherein the cDNA of the recombinant viral RNA has at least an N gene, an X gene, a P gene and an L gene of the Borna disease viral genome in the same order as in the Borna disease viral genome and has an inserted foreign gene;

(b) DNAs encoding ribozymes; and (c) a promoter sequence, wherein (b) the DNAs encoding ribozymes are located upstream and downstream of (a) the cDNA of the recombinant viral RNA, and (a) the cDNA of the recombinant viral RNA and (b) the DNAs encoding ribozymes are located downstream of (c) the promoter sequence.

(3) The viral vector according to the above (2), wherein (a) the cDNA of the recombinant viral RNA further has a disrupted M gene of the Borna disease viral genome.

(4) The viral vector according to the above (2), wherein (a) the cDNA of the recombinant viral RNA has the foreign gene inserted in an untranslated region between open reading frames of the P gene and the M gene of the Borna disease viral genome.

(5) The viral vector according to any one of the above (2) to (4), wherein (c) the promoter sequence is an RNA polymerase II promoter sequence.

(6) The viral vector according to any one of the above (2) to (5), wherein (b1) a cDNA encoding a hammer head ribozyme is located upstream of (a) the cDNA of the recombinant viral RNA, and (b2) a cDNA sequence encoding a hepatitis δ virus ribozyme is located downstream of (a) the cDNA of the recombinant viral RNA.

(7) The viral vector according to any one of the above (2) to (6), wherein (a) the cDNA of the recombinant viral RNA comprises:

restriction enzyme sites at the 3' and 5' ends of the foreign gene;

a sequence of SEQ ID NO: 9 located between the restriction enzyme site at the 3' end of the foreign gene and the open reading frame of the P gene and a sequence of SEQ ID NO: 9 located between the restriction enzyme site at the 5' end of the foreign gene and the open reading frame of the L gene, or when the cDNA of the recombinant viral RNA has the M gene of the Borna disease viral genome in the same location as in the Borna disease viral genome, a sequence of SEQ ID NO: 9 located between the restriction enzyme site at the 3' end of the foreign gene and the open reading frame of the P gene and a sequence of SEQ ID NO: 9 located between the restriction enzyme site at the 5' end of the foreign gene and the open reading frame of the M gene;

at least an inserted nucleotide sequence cc between the restriction enzyme site at the 3' end of the foreign gene and the sequence of SEQ ID NO: 9 located near the 3' end of the foreign gene; and at least an inserted nucleotide sequence cca between the restriction enzyme site at the 5' end of the foreign gene and the sequence of SEQ ID NO: 9 located near the 5' end of the foreign gene.

(8) A recombinant virus comprising an RNA encoded by the viral vector according to any one of the above (1) to (7).

(9) A method for preparing a recombinant virus, the method comprising the steps of:

introducing into a cell in vitro the viral vector according to any one of the above (1) to (7) together with a plasmid or plasmids expressing an N gene, a P gene and an L gene of a Borna disease viral genome and a G gene of an avian bornaviral genome as a helper plasmid or helper plasmids, and culturing the cell having the viral vector and the helper plasmid or helper plasmids introduced therein to produce a recombinant virus.

(10) A method for preparing a recombinant virus, the method comprising the steps of:

introducing into a cell in vitro the viral vector according to any one of the above (1) to (7) together with a plasmid or plasmids expressing an N gene, a P gene and an L gene of a Borna disease viral genome and with a plasmid expressing a G gene of an avian bornaviral genome as helper plasmids, and culturing the cell having the viral vector and the helper plasmids introduced therein to produce a recombinant virus.

(11) The method for preparing a recombinant virus according to the above (9) or (10), further comprising introducing a plasmid expressing an M gene of a Borna disease viral genome as a helper plasmid into the cell in vitro.

(12) A method for introducing a foreign gene, the method comprising the step of infecting a cell or an animal with the recombinant virus according to the above (8) or a recombinant virus prepared by the method according to any one of the above (9) to (11).

(13) A foreign gene introducing agent comprising the recombinant virus according to the above (8) or a recombinant virus prepared by the method according to any one of the above (9) to (11).

(14) A foreign gene introducing agent for cranial nerve cells, the agent comprising the recombinant virus according to the above (8) or a recombinant virus prepared by the method according to any one of the above (9) to (11).

(15) A kit for introducing a foreign gene, the kit comprising the viral vector according to any one of the above (1) to (7).

The present invention also includes the following methods, uses, etc.

A method for introducing a foreign gene into a cranial nerve cell, the method comprising administering to an animal the recombinant virus according to (8) or a recombinant virus prepared by the method according to any one of (9) to (11).

A use of the recombinant virus according to (8) or a recombinant virus prepared by the method according to any one of (9) to (11) for production of a foreign gene introducing agent.

A use of the recombinant virus according to (8) or a recombinant virus prepared by the method according to any one of (9) to (11) for production of a foreign gene introducing agent for a cranial nerve cell.

The recombinant virus according to (8) or a recombinant virus prepared by the method according to any one of (9) to (11) for use in introduction of a foreign gene into a cell or an animal in vitro.

The recombinant virus according to (8) or a recombinant virus prepared by the method according to any one of (9) to (11) for use in introduction of a foreign gene into a cranial nerve cell.

Advantageous Effects of Invention

The present invention enables the preparation of a viral vector that has a wide host range for infection, has high efficiency of introduction of a foreign gene, is safe due to no integration of the viral genome into a host chromosome, has high stability and high persistency in host cells due to expression of a foreign gene with no cytotoxicity in the cell nucleus, is capable of preferentially introducing a foreign gene into cells of interest such as cranial nerve cells, and is capable of producing a low pathogenic (highly safe) recombinant virus with high productivity due to transmissibility only to cells of interest. The present invention also enables the preparation of such a recombinant virus. The present invention further enables the preferential and efficient introduction of a foreign gene into cells of interest such as cranial nerve cells, and enables the persistent expression of the foreign gene in the cells. In addition, the recombinant virus produced from the viral vector of the present invention causes persistent infection in the nucleus of cells such as cranial nerve cells, and therefore the recombinant virus is hardly attacked and eliminated by host immunity. Further, the P protein contained in the recombinant virus of the present invention functions to suppress host immune response pathways, and consequently natural immunity is not activated by the virus-infected cells.

BRIEF DESCRIPTION OF DRAWINGS

FIG. 8 shows representative images taken under a microscope, showing protein expression in cells infected with wild-type BDV or a recombinant virus (left panels), and a chart showing the number of GFP-positive cells in the same experiment (right panel).

DESCRIPTION OF EMBODIMENTS

Figure 1:
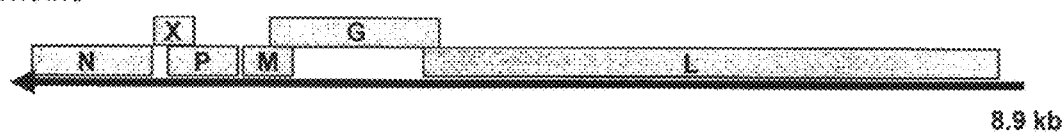
FIG. 1 is a schematic view of the structure of a Borna disease virus genome (wild-type).

The present invention relates to a bornaviral vector comprising a cDNA of a recombinant viral RNA having a sequence of a Borna disease viral genome comprising a disrupted G gene of the Borna disease viral genome and an inserted G gene of an avian bornaviral genome. The viral vector is capable of efficiently introducing a foreign gene. The viral vector of the present invention may have or may not have a foreign gene because a foreign gene can be introduced into the viral vector by a known technique after the preparation of the viral vector. Borna disease virus generally includes those contain various genes in a different alignment, but for ease of convenience, the present invention will be described based on a Borna disease virus suitable for the bornaviral vector of the present invention. It should be noted that the present invention is not limited to the Borna disease virus.

1. Viral Vector

A preferred viral vector of the present invention comprises: (a) a cDNA of a recombinant viral RNA having a sequence of a Borna disease viral genome comprising a disrupted G gene of the Borna disease viral genome and an inserted G gene of an avian bornaviral genome, wherein the cDNA of the recombinant viral RNA has at least an N gene, an X gene, a P gene and an L gene of the Borna disease viral genome in the same order as in the Borna disease viral genome and has an inserted foreign gene; (b) DNAs encoding ribozymes; and (c) a promoter sequence, wherein (b) the DNAs encoding ribozymes are located upstream and downstream of (a) the cDNA of the recombinant viral RNA, and (a) the cDNA of the recombinant viral RNA and (b) the DNAs encoding ribozymes are located downstream of (c) the promoter sequence. This viral vector is called the viral vector of the aspect A.

The above (a) cDNA of the recombinant viral RNA is hereinafter simply called "(a) the cDNA of the recombinant BDV genome". The viral vector according to the aspect A may also contain another sequence in addition to the above (a), (b) and (c) as long as the viral vector exerts the effects according to the present invention.

(a) cDNA of Recombinant BDV Genome

In the aspect A, (a) the cDNA of the recombinant BDV genome has a sequence of a Borna disease viral genome (BDV genome) comprising a disrupted G gene of the BDV genome, an inserted foreign gene and an inserted G gene of an avian bornaviral genome (ABV genome) (hereinafter may also called G' gene) having a different genotype from that of the disrupted G gene, wherein the cDNA of the recombinant BDV genome has at least an N gene, an X gene, a P gene and an L gene of the BDV genome in the same order as in the BDV genome.

The "destructed gene" typically means that a gene does not exist in a form that allows the gene to encode a protein (for example, the G protein in the case where the gene is the G gene). Destruction of a gene can be performed by deleting the whole gene, deleting a part of a gene, inserting another sequence into a gene, replacing an amino acid in a gene with another amino acid, or other methods.

The BDV genome in the present invention, including the aspect A, may be any gene of a bornavirus belonging to the species Mammalian 1 bornavirus of the genus Bornavirus of the family Bornaviridae, or a mutant thereof. The species Mammalian 1 bornavirus includes, besides others, Borna disease virus 1 (BDV-1) and Borna disease virus 2 (BDV-2). In particular, for example, the virus strains He80, H1766, Strain V, huP2br, etc., as well as the mutant stains No/98, Bo/04w and HOT6 can be used. These genome sequences are available from, for example, the following.

He80: GenBank Accession #L27077, Cubitt, B., Oldstone, C. and de la Torre, J. C. Sequence and genome organization of Borna disease virus. J. Virol. 68 (3), 1382-1396 (1994).

H1766: GenBank Accession #AJ311523, Pleschka, S., Staeheli, P., Kolodziejek, J., Richt, J. A., Nowotny, N. and Schwemmle, M. Conservation of coding potential and terminal sequences in four different isolates of Borna disease virus. J. Gen. Virol. 82 (PT 11), 2681-2690 (2001).

Strain V: GenBank Accession #U04608, Briese, T., Schneemann, A., Lewis, A. J., Park, Y. S., Kim, S., Ludwig, H. and Lipkin, W. I. Genomic organization of Borna disease virus. Proc. Natl. Acad. Sci. U.S.A. 91 (10), 4362-4366 (1994).

huP2br: GenBank Accession #AB258389, Nakamura, Y., Takahashi, H., Shoya, Y., Nakaya, T., Watanabe, M., Tomonaga, K., Iwahashi, K., Ameno, K., Momiyama, N., Taniyama, H., Sata, T., Kurata, T., de la Torre, J. C., Ikuta, K. Isolation of Borna disease virus from human brain tissue, J. Virol 74 (2000) 4601-4611.

No/98: GenBank Accession #AJ311524, Nowotny, N. and Kolodziejek, J. Isolation and characterization of a new subtype of Borna disease virus. J. Gen. Virol. 74, 5655-5658 (2000).

Bo/04w: GenBank Accession #AB246670, Watanabe, Y., Ibrahim, M. S., Hagiwara, K., Okamoto, M., Kamitani, W., Yanai, H., Ohtaki, N., Hayashi, Y., Taniyama, H., Ikuta, K. and Tomonaga, K. Characterization of a Borna disease virus field isolate which shows efficient viral propagation and transmissibility. Microbes and Infection 9 (2007) 417-427.

The ABV genome in the present invention, including the aspect A, may be any gene of an avian infectious bornavirus belonging to the genus Bornavirus of the family Bornaviridae, or a mutant thereof. Avian bornavirus displays a high genetic variability, and includes, for example, Psittaciform 1 bornavirus, including Parrot bornavirus 1 (PaBV-1), Parrot bornavirus 2 (PaBV-2), Parrot bornavirus 3 (PaBV-3), Parrot bornavirus 4 (PaBV-4), Parrot bornavirus 7 (PaBV-7), etc.; Psittaciform 2 bornavirus, including Parrot bornavirus 5 (PaBV-5) etc.; Passeriform 1 bornavirus, including Canary bornavirus 1 (CnBV-1), Canary bornavirus 2 (CnBV-2), Canary bornavirus 3 (CnBV-3), etc.; Passeriform 2 bornavirus, including Estrildid finch bornavirus 1 (EsBV-1) etc.; and Waterbird 1 bornavirus, including Aquatic bird bornavirus 1 (ABBV-1), Aquatic bird bornavirus 2 (ABBV-2), etc. Besides these, avian bornavirus also includes Parrot bornavirus 6 (PaBV-6), Parrot bornavirus 8 (PaBV-8), Munia bornavirus 1 (MuBV-1), etc. The ABV species can be phylogenetically classified: Psittaciform 2 bornavirus, Passeriform 1 bornavirus, Passeriform 2 bornavirus, Waterbird 1 bornavirus and Waterbird 2 bornavirus are clustered into Clade 2; and Psittaciform 1 bornavirus belongs to Clade 3 (see Komorizono R. et al., Microbiol Immunol 60:437-441 (2016)). In particular, for example, the ABV strains PaBV-1, PaBV-2, PaBV-3, PaBV-4, PaBV-5, CnBV-1, CnBV-2, EsBV-1, ABBV-1, ABBV-2, MuBV-1, etc., as well as mutant strains thereof can be used. The genome sequences of these strains are available from, for example, international nucleotide sequence databases under the following accession numbers: PaBV-1: GU249595, PaBV-2: EU781967, PaBV-3: FJ169440, PaBV-4: JN014948, PaBV-7: JX065210, PaBV-5: KR612223, CnBV-1: KC464471, CnBV-2: KC464478, CnBV-3: KC595273, EsBV-1: KF680099, ABBV-1: KF680099, ABBV-2: KJ756399, PaBV-6: FJ794743, and PaBV-8: KJ950625.

Some of the nucleotides of the BDV genome sequence and the ABV genome sequence may be replaced with another nucleotide, deleted, or interrupted by a nucleotide insertion, or some parts of the nucleotide sequence may be transposed, as long as the functions as a bornavirus are maintained. Such derivatives can be used for the present invention. The above "part" or "parts" may be, for example, in terms of the amino acid residues, one to several (usually 1 to 5, preferably 1 to 3, more preferably 1 or 2) amino acid residues.

In the aspect A, the recombinant BDV genome that has a disrupted G gene, an inserted G gene of an ABV genome and an inserted foreign gene and has at least the N gene, the X gene, the P gene and the L gene of the BDV genome in the same order as in the BDV genome may further comprise an M gene of a BDV genome. In this embodiment, the M gene is located in the same location as in the BDV genome.

The G gene of an ABV genome in the present invention, including the aspect A, may be any G gene having a different genotype from that of the G gene in the original BDV genome before gene editing, and may be selected as appropriate depending on the type of the original BDV genome before gene editing. In particular, for example, when the original BDV genome before gene editing is the genome of Borna disease virus 1 (BDV-1), the G gene of an ABV genome to be inserted may be the G gene of an ABV belonging to Clade 2 or Clade 3 of the genus Bornavirus. Specifically, the G gene of Parrot bornavirus 2 (PaBV-2), the G gene of Parrot bornavirus 4 (PaBV-4), the G gene of Parrot bornavirus 5 (PaBV-5), the G gene of Munia bornavirus 1 (MuBV-1), etc. can be used alone or in combination of two or more types. Alternatively, a partial fusion protein of the G gene of an ABV genome and the G gene of a BDV genome (chimera gene) that retains the original functions of the G gene of an ABV genome may be used.

The insertion site for the G gene of an ABV genome is not limited, but, for example, in the aspect A, the G gene of an ABV genome may be inserted into the untranslated region immediately downstream of the open reading frame of the P gene of a BDV genome, or when the recombinant BDV genome has the M gene of a BDV genome in the same location as in the BDV genome, the G gene of an ABV genome may be inserted into the untranslated region immediately downstream of the open reading frame of the M gene, or the G gene of an ABV genome may be inserted into the untranslated region immediately downstream of the open reading frame of the L gene of a BDV genome, etc.

The type and length of a foreign gene in the present invention are not limited, and any desired gene can be used depending on the purpose. Examples of the foreign gene include a cDNA of a gene encoding a protein or a peptide; a cDNA encoding an siRNA, a short hairpin RNA (shRNA) or a microRNA (miRNA); and a cDNA encoding an RNA aptamer. For the viral vector of the present invention, one or more foreign genes can be used.

Figure 2A:
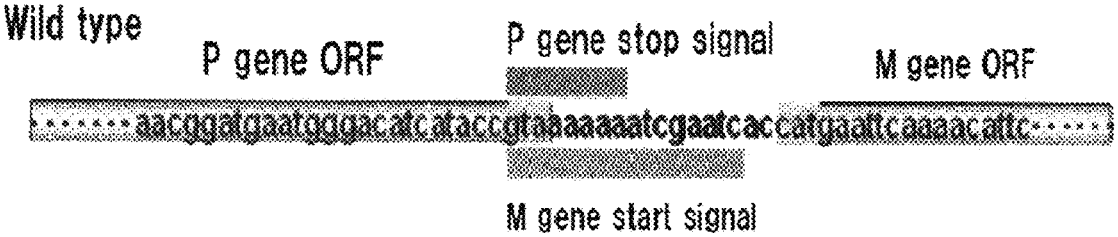
FIG. 2A is a schematic view of the untranslated region between the ORF of the P gene and the ORF of the M gene in the cDNA of a wild-type BDV genome (positions 1875 to 1895 in the nucleotide sequence of the BDV genome).

The insertion site for a foreign gene is not limited, but, for example, in the aspect A, a foreign gene is preferably inserted into the untranslated region immediately downstream of the open reading frame of the P gene of a BDV genome. Alternatively, when the recombinant BDV genome has the M gene of a BDV genome in the same location as in the BDV genome, a foreign gene is preferably inserted into the untranslated region between the open reading frame of the P gene and the open reading frame of the M gene. Insertion of a foreign gene in such a region enhances the productivity of a recombinant virus from the viral vector, i.e., enhances the replicative efficiency of a recombinant virus produced from the viral vector, thereby allowing efficient production of the recombinant virus. Further, the recombinant virus produced from (replicated by) the viral vector efficiently expresses the foreign gene after introduction into cells. Therefore, introduction of the viral vector of the present invention into cells, or infection of cells with recombinant BDV particles produced from the viral vector allows efficient introduction of a foreign gene into the cells, and in turn allows efficient expression of the foreign gene in the cells. As shown in FIG. 2A, in the cDNA of the wild-type BDV genome, the stop signal sequence of the P gene (positions 1875 to 1882 of SEQ ID NO: 1) and the start signal sequence of the M gene (positions 1875 to 1890 of SEQ ID NO: 1) are present in the untranslated region immediately downstream of the ORF of the P gene (i.e., the untranslated region between the P gene and the M gene in the BDV genome) (for example, positions 1875 to 1895 of the cDNA sequence of the BDV genome of SEQ ID NO: 1 (i.e., the nucleotides at positions 1875 to 1895 of SEQ ID NO: 1)). The insertion site for a foreign gene within the untranslated region between the open reading frame of the P gene and the open reading frame of the M gene (for example, positions 1878 and 1892 of SEQ ID NO: 1) is preferably the region excluding the stop signal sequence of the P gene and/or the start signal sequence of the M gene, more preferably the region excluding the stop signal sequence of the P gene and the start signal sequence of the M gene. For example, when a foreign gene is inserted into the cDNA sequence of the BDV genome of SEQ ID NO: 1, the foreign gene is further preferably inserted into the region between positions 1890 and 1891 of SEQ ID NO: 1. When the insertion site for the G gene of an ABV genome and the insertion site of a foreign gene are contained in the same region, either of the G gene of an ABV genome or the foreign gene may be present upstream of the other, or the G gene of an ABV genome and the foreign gene may be inserted in this order, or the foreign gene and the G gene of an ABV genome may be inserted in this order. When two or more foreign genes are used, they may be inserted into separate regions or may be inserted in the same region.

A restriction enzyme site may be present at one end or both ends (preferably both ends) of an inserted foreign gene. One or more restriction enzyme sites are preferably contained in the BDV genome sequence because a foreign gene can be easily integrated into the BDV genome sequence and the efficiency of protein translation of a foreign gene is increased. In the present invention, examples of the restriction enzyme sites that can be located at one end or both ends of a foreign gene include Bst BI, Pac I, Sse8387 I, Swa I and Kpn I sites for the 3' end of a foreign gene, preferably a Bst BI site; and Pac I, Bst BI, Sse8387 I, Swa I and Kpn I sites for the 5' end of a foreign gene, preferably a Pac I site.

Figure 2B:
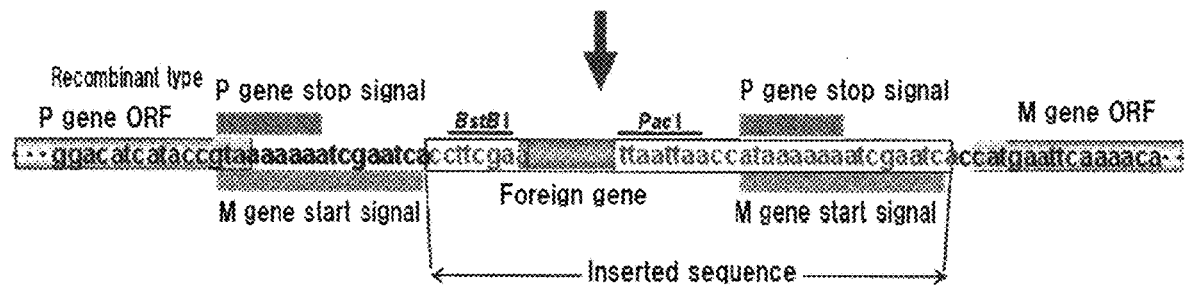
FIG. 2B is a schematic view showing an example of the insertion site for a foreign gene in a viral vector of the present invention.

In cases where the recombinant BDV genome in the aspect A contains the M gene, the cDNA of the recombinant BDV genome preferably contains a sequence containing a P gene stop signal sequence and a M gene start signal sequence (taaaaaaatcgaatca (SEQ ID NO: 9) both in the region between a foreign gene (including as needed a restriction enzyme site at one end or both ends thereof) and the ORF of the P gene and in the region between the foreign gene (including as needed a restriction enzyme site at one end or both ends thereof) and the ORF of the M gene. In the cDNA of the recombinant BDV genome in the present invention, for example, a foreign gene is preferably inserted in the position as shown in FIG. 2B. FIG. 2B shows an example of the cDNA of the recombinant BDV genome containing the M gene. Also in cases where the M gene is deleted, the cDNA of the recombinant BDV genome preferably has a sequence containing the P gene stop signal sequence and the M gene start signal sequence (SEQ ID NO: 9) downstream of a foreign gene, as shown in FIG. 2B. In cases where the M gene is deleted, the P gene stop signal sequence and the M gene start signal sequence downstream of a foreign gene, as shown in FIG. 2B, function as a stop signal for the foreign gene and as a start signal for the L gene, respectively. FIG. 2B shows an example of an embodiment where a Bst BI site and a Pac I site are inserted in the 3' end and the 5' end of a foreign gene, respectively, but the restriction enzyme sites at both ends of a foreign gene are not limited thereto.

In the above manner, the location of each gene in the recombinant BDV genome of the aspect A can be determined.

The cDNA of the recombinant BDV genome as described above includes, in addition to the cDNA encoding the sequence in which the genes are located as described above, a cDNA of a RNA having the sequence in which the genes are located as described above, and a cDNA of a recombinant viral RNA having the sequence in which the genes are located as described above. Preferred embodiments of (a) the cDNA of the recombinant BDV genome of the aspect A are schematically shown in FIGS. 3A to 5B.

Figure 3A:
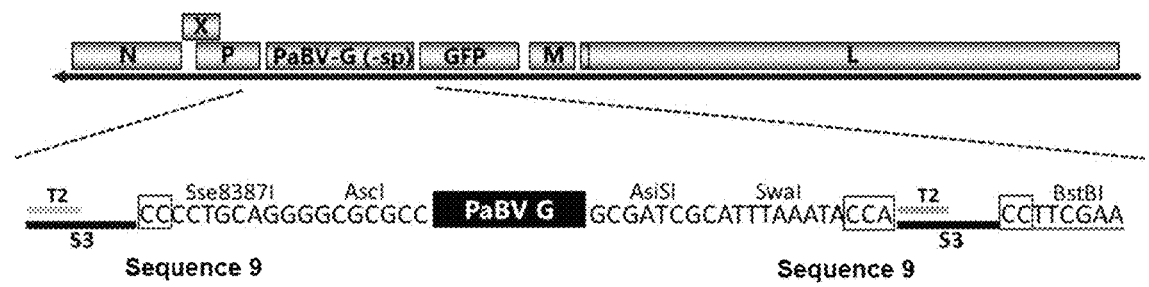
FIGS. 3A and 3B are schematic views showing an example of the structure of an RNA sequence from which a viral vector of the present invention is prepared.
Figure 3B:
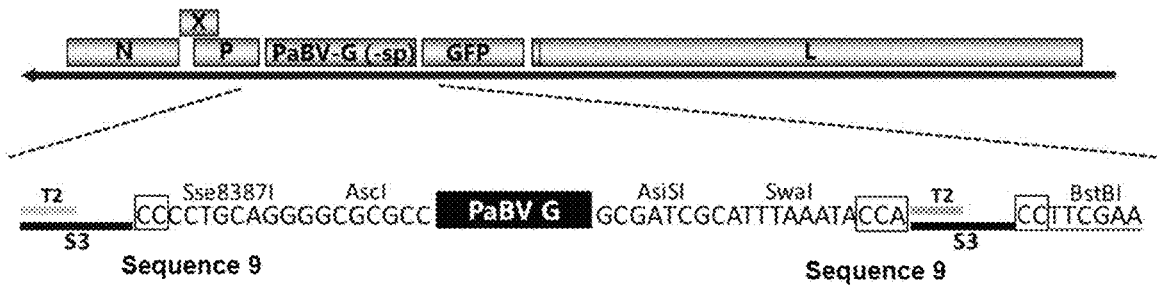

FIG. 3A shows a cDNA of a recombinant BDV genome having a sequence in which the G gene is disrupted (deleted) and the G' gene and a foreign gene (GFP in FIGS. 3A and 3B) are inserted in this order in the untranslated region between the open reading frame of the P gene and the open reading frame of the M gene (aspect 1-1). FIG. 3B shows another aspect of the cDNA of the aspect 1-1 in which the M gene is disrupted (deleted) (aspect 1-2).

Figure 4A:
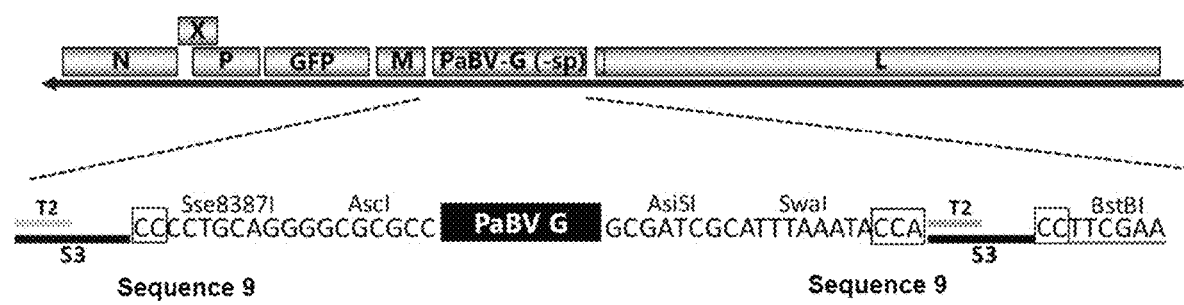
FIGS. 4A and 4B are schematic views showing an example of the structure of an RNA sequence from which a viral vector of the present invention is prepared.
Figure 4B:
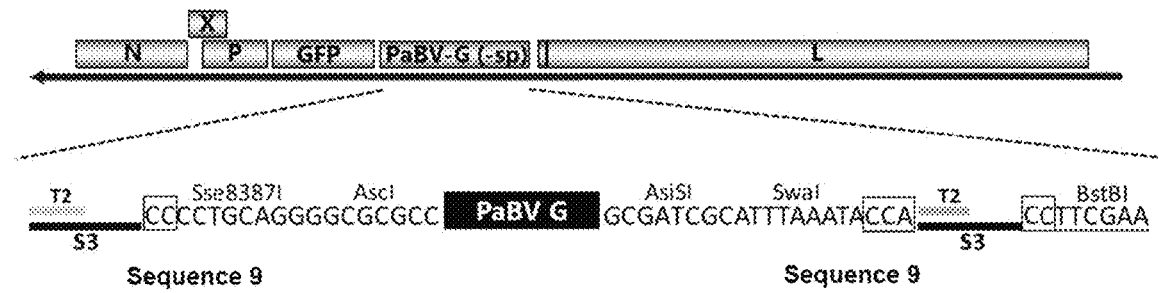

FIG. 4A shows a cDNA of a recombinant BDV genome having a sequence in which the G gene is disrupted (deleted), and a foreign gene (GFP in FIGS. 4A and 4B) is inserted in the untranslated region between the open reading frame of the P gene and the open reading frame of the M gene, and the G' gene is inserted in the untranslated region immediately downstream of the open reading frame of the M gene (aspect 2-1). FIG. 4B shows another aspect of the cDNA of the aspect 2-1 in which the M gene is disrupted (deleted), and in this aspect, a foreign gene and the G' gene are inserted in this order in the untranslated region immediately downstream of the open reading frame of the P gene (aspect 2-2).

Figure 5A:
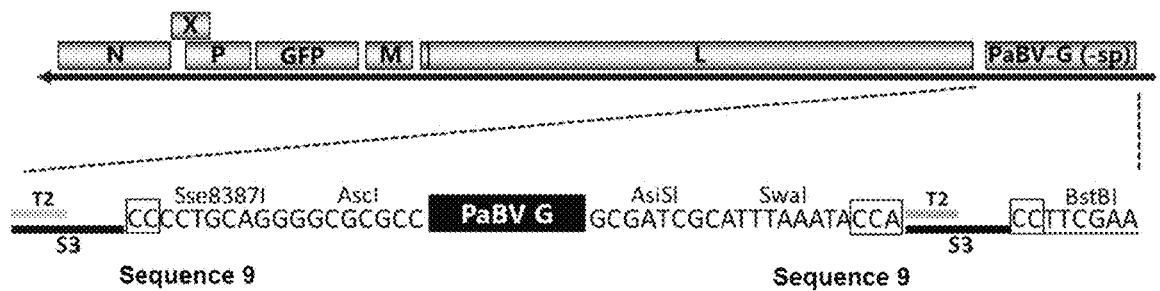
FIGS. 5A and 5B are schematic views showing an example of the structure of an RNA sequence from which a viral vector of the present invention is prepared.
Figure 5B:
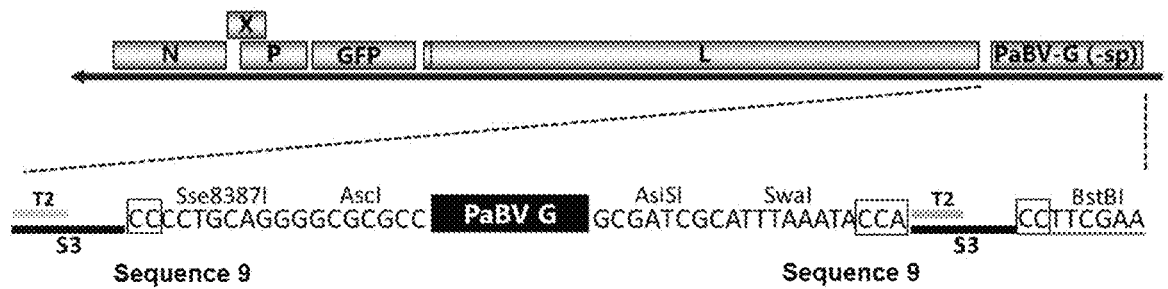

FIG. 5A shows a cDNA of a recombinant BDV genome having a sequence in which the G gene is disrupted (deleted), and a foreign gene (GFP in FIGS. 5A and 5B) is inserted in the untranslated region between the open reading frame of the P gene and the open reading frame of the M gene, and the G' gene is inserted in the untranslated region immediately downstream of the open reading frame of the L gene (aspect 3-1). FIG. 5B shows another aspect of the cDNA of the aspect 3-1 in which the M gene is disrupted (deleted) (aspect 3-2).

The L gene in a natural BDV genome is interrupted by the presence of the G gene. The G gene in the recombinant BDV genome of the aspect A may be deleted together with the intron of the L gene, and the exons of the open reading frame (ORF) of the L gene may be spliced together, thereby leading to enhanced replication ability of a recombinant virus, i.e., the enhanced expression efficiency of a foreign gene in cells. The deletion of the intron of the L gene also makes possible the insertion of a larger foreign gene. The deletion of the intron of the L gene can be performed by a known method.

The recombinant BDV genome of the aspect A from which the M gene is deleted, corresponding to a natural BDV genome from which the G gene and the M gene are deleted, produces a recombinant virus with reduced pathogenicity, which is much more safer.

The cDNA of the recombinant BDV genome can be prepared based on the viral genome information. For example, the cDNA can be prepared from a RNA genome using a reverse transcriptase. The cDNA can also be chemically synthesized using a DNA synthesizer based on the desired sequence. Alternatively, the cDNA can also be prepared by an amplification technique known in the art, such as PCR. Procedures such as PCR and primer preparation can be carried out by a gene engineering technique (a genetic manipulation technique) known in the art.

(b) DNAs Encoding Ribozymes

The DNAs encoding ribozymes may have any sequence encoding a ribozyme that can cleave a foreign gene transcribed from (a) the cDNA of the recombinant virus. Examples of (b) the DNAs encoding ribozymes include DNAs including a cDNA encoding a ribozyme, such as a hammer head ribozyme (HamRz), a hepatitis δ virus ribozyme (HDVRz), a hairpin ribozyme, and an artificial ribozyme. Besides these, a DNA such as a cDNA encoding a modified form of the above ribozyme that retains ribozyme activity can also be used. Examples of the modified ribozyme include a polynucleotide that has a nucleotide sequence containing the consensus sequence and substitution, deletion or addition of one to several ("several" means, for example, 10, preferably 5, more preferably 3, further preferably 2) nucleotides, and functions as a ribozyme. Preferred ribozymes in the present invention are a hammer head ribozyme (HamRz) and a hepatitis δ virus ribozyme (HDVRz). More preferably, (b1) a DNA (preferably a cDNA) encoding HamRz is located upstream of, i.e., at the 3' end of, (a) the cDNA of the recombinant BDV genome, and (b2) a DNA (preferably a cDNA) sequence encoding HDVRz is located downstream of, i.e., at the 5' end of, (a) the cDNA of the recombinant BDV genome. This enhances the efficiency of expression of a foreign gene in cells.

The nucleotide sequence of HamRz is described in Yanai et al., Microbes and Infections 8 (2006) 1522-1529; Mercier et al., J. Virol. 76 (2002) 2024-2027; Inoue et al., J. Virol. Methods 107 (2003) 229-236; etc.

The nucleotide sequence of HDVRz is described in Ferre-D'Amare, A. R., Zhou, K. and Doudna, J. A. Crystal structure of a hepatitis δ virus ribozyme. Nature 395 (6702), 567-574 (1998); etc.

A cDNA encoding the HamRz nucleotide sequence and a cDNA encoding the HDVRz nucleotide sequence described in these literatures can be used in the present invention. Preferred nucleotide sequences of HamRz and HDVRz in the present invention are shown below.

HamRz:
(SEQ ID NO: 2)
5'-UUGUAGCCGUCUGAUGAGUCCGUGAGGACGAAACUAUAGGAAAGGAAU
UCCUAUAGUCAGCGCUACAACAAA-3'

HDVRz:
(SEQ ID NO: 3)
5'-GGCCGGCAUGGUCCCAGCCUCCUCGCUGGCGCCGGCUGGGCAACACCA
UUGCACUCCGGUGGCGAAUGGGAC-3'

(c) Promoter Sequence (c) The promoter sequence in the present invention may be an RNA polymerase II promoter sequence, an RNA polymerase I promoter sequence, or a T7 polymerase promoter sequence. Preferred is an RNA polymerase II promoter sequence. Examples of the RNA polymerase II promoter include a CMV promoter and a CAGGS promoter. Preferred is a CAGGS promoter. These promoter sequences are described in, for example, J. A. Sawicki, R. J. Morris, B. Monks, K. Sakai, J. Miyazaki, A composite CMV-IE enhancer/b-actin promoter is ubiquitously expressed in mouse cutaneous epithelium, Exp. Cell Res. 244 (1998) 367-369.

The locations of (a) the cDNA of the recombinant BDV genome, (b) the DNAs encoding ribozymes and (c) the promoter sequence in the viral vector of the aspect A are not limited as long as (b) the DNAs encoding ribozymes are located upstream and downstream of (a) the cDNA of the recombinant BDV genome, and (a) the cDNA of the recombinant BDV genome and (b) the DNAs encoding ribozymes are located downstream of (c) the promoter sequence. In a preferred aspect, (b1) a cDNA encoding a hammer head ribozyme is located upstream of (a) the cDNA of the recombinant BDV genome, and (b2) a cDNA sequence encoding a hepatitis δ virus ribozyme is located downstream of (a) the cDNA of the recombinant BDV genome. In another aspect, (a) the cDNA of the recombinant BDV genome and (b) the DNAs encoding ribozymes are located downstream of (c) the RNA polymerase II promoter. In another aspect, (b1) a cDNA encoding a hammer head ribozyme is located upstream of (a) the cDNA of the recombinant BDV genome, (b2) a cDNA sequence encoding a hepatitis δ virus ribozyme is located downstream of (a) the cDNA of the recombinant BDV genome, and (a) the cDNA of the recombinant BDV genome and (b1) a cDNA encoding a hammer head ribozyme are located downstream of (c) the RNA polymerase II promoter.

(d) Other Nucleotide Sequences

The viral vector of the present invention including the aspect A can contain the whole or part of SV40 virus replication origin/promoter region sequence, in addition to the above DNAs (a), (b) and (c). In cases where the viral vector contains the whole or part of SV40 virus replication origin/promoter region sequence, the sequence is preferably located downstream of (a) the cDNA of the recombinant BDV genome and (b) the DNAs encoding ribozymes. The part of the SV40 virus DNA replication origin/promoter region sequence is preferably a fragment consisting of 113 nucleotides at the 5' end of the SV40 replication origin/promoter region.

The SV40 virus replication origin/promoter region sequence (SEQ ID NO: 4) is described in, for example, D. A. Dean, B. S. Dean, S. Muller, L. C. Smith, Sequence requirements for plasmid nuclear import, Exp. Cell. Res. 253 (1999) 713-722, etc.

The viral vector of the present invention can further contain one or more factors that are advantageous to protein expression, for example, one or more of nucleic acid sequences encoding an enhancer, an activator (for example, a transactivator), a chaperon, and a processing protease, as long as the viral vector exerts the effects according to the present invention. The viral vector of the present invention may also have a factor that is functional in selected cells.

The viral vector of the present invention may be a linear DNA or a circular DNA, but when the viral vector is introduced into cells, the viral vector is preferably in a circular form. Examples of the circular viral vector include a commercially available plasmid vector in which the above DNAs (a), (b) and (c) essential for the viral vector of the aspect A and the optional DNA (d) are located in the above-described predetermined order. The commercially available plasmid vector may be any virus vector that can replicate itself in cells into which the virus vector is to be introduced. Examples of the vector include pBluescript SKII (–), pCAGGS, pCXN2, and pCDNA3.1.

2. Preparation Method of Viral Vector

The preparation method of the viral vector of the present invention is not limited to a particular one, and may be any gene engineering method known in the art. For example, the self-replicating (persistently infecting) viral vector of the aspect A of the present invention can be prepared as follows, in accordance with the method described in 2.2 Plasmid construction in "Materials and methods" in Yanai et al., Microbes and Infection 8 (2006) 1522-1529. A viral vector is first prepared by replacing the CAT gene with the sequence of a BDV genome and inserting a foreign gene of interest into the untranslated region immediately downstream of the P gene (the untranslated region between the P gene and the M gene). PCR or other methods are performed using this vector as a template to introduce a deletion mutation etc. into the G gene of the viral vector to give a viral vector lacking the G gene (also called the G gene-deficient BDV viral vector). Then, the G gene of an ABV genome is inserted into the desired region of the G gene-deficient BDV viral vector to give the self-replicating (persistently infecting) viral vector of the present invention. When the G gene of an ABV genome is inserted upstream of a foreign gene, the viral vector prepared as described above has, for example, (a) the cDNA of the recombinant viral RNA encoding of a BDV genome containing the G gene of an ABV genome and a foreign gene in this order in the untranslated region between the open reading frame of the P gene and the open reading frame of the M gene (for example, the cDNA of the recombinant virus having the structure schematically shown in FIG. 3A). Preferably, in the preparation of the G gene-deficient BDV viral vector, the intron of the L gene can also be deleted by PCR. Similarly, the M gene can also be deleted by PCR etc. using the G gene-deficient BDV viral vector as a template (the resulting viral vector is also called the G gene- and M gene-deficient BDV viral vector).

The viral vector in a linear form can be prepared from the above circular viral vector by selecting a restriction enzyme as appropriate for the type of the vector so that the enzyme can cleave one region other than the region of (a) the cDNA of the recombinant BDV genome, (c) the promoter sequence or other signal sequences necessary for protein expression; and cleaving the circular viral vector with the restriction enzyme.

Examples of a method for introducing a foreign gene contained in the viral vector of the present invention into cells of interest include a method involving introduction of the viral vector together with one or more helper plasmids described below into cells of interest; and a method involving infection of cells of interest with a recombinant virus produced from the viral vector. Preferred is the method using a recombinant virus produced from the viral vector. The recombinant virus produced from the viral vector of the present invention is a recombinant BDV having an RNA encoded not by a wild-type BDV genome but by the above viral vector.

3. Recombinant Virus

A recombinant virus containing the RNA encoded by the above viral vector is also one aspect of the present invention. When the viral vector of the aspect A is used, the recombinant virus preferably contains the RNA encoded by the viral vector, the N protein of a BDV, the P protein of a BDV, the L protein of a BDV, and the G protein of an ABV. The recombinant virus of the present invention contains the above recombinant BDV genome and thereby functions as a persistently infecting recombinant virus that persistently expresses a foreign gene after infection to cells. The recombinant virus may contain the M protein of a BDV as desired.

The recombinant virus of the present invention can be prepared by, for example, a method comprising the steps of: introducing into a cell in vitro the viral vector as described above together with a plasmid or plasmids expressing the N gene, the P gene and the L gene of a BDV genome and the G gene of an ABV genome as a helper plasmid or helper plasmids, and culturing the cell having the viral vector and the helper plasmid or helper plasmids introduced therein to produce a recombinant virus. According to the present invention, for example, each gene of the recombinant BDV genome may be contained in a separate helper plasmid and introduced together with the viral vector of the aspect A into a cell to produce the recombinant virus containing the recombinant BDV genome. For example, a plasmid or plasmids expressing the N gene, the P gene and the L gene of a BDV genome can be introduced together with a plasmid expressing the G gene of an ABV genome as helper plasmids. That is, the recombinant virus can be prepared by a method comprising the steps of introducing into a cell in vitro the G gene-deficient BDV viral vector not having the G gene of an ABV genome together with a plasmid or plasmids expressing the N gene, the P gene and the L gene of a BDV genome and with a plasmid expressing the G gene of an ABV genome as helper plasmids, and culturing the cell having the viral vector and the helper plasmids introduced therein to produce a recombinant virus. Such a preparation method of the recombinant virus is also one aspect of the present invention. In the above manner, the recombinant virus can be produced in vitro. The cell in vitro into which the viral vector and the helper plasmid or helper plasmids are to be introduced is usually a cultured cell.

When the G gene- and M gene-deficient BDV viral vector is used as the viral vector of the aspect A, a plasmid expressing the M gene of a BDV genome is preferably further introduced as a helper plasmid into the cell. That is, when the G gene- and M gene-deficient BDV viral vector is used, a plasmid or plasmids expressing the N gene, the P gene and the L gene of the BDV genome and the G gene of an ABV genome can be introduced together with a plasmid expressing the M gene of a BDV genome into the cell in vitro, or alternatively, a plasmid or plasmids expressing the N gene, the P gene and the L gene of the BDV genome and a plasmid expressing the G gene of an ABV genome can be introduced together with a plasmid expressing the M gene of a BDV genome into the cell in vitro.

The helper plasmid or helper plasmids may be any plasmid or plasmids that express the N gene, the P gene and the L gene and/or the M gene of a BDV genome, and/or the G gene of an ABV. Two or more of these genes may be contained in a single plasmid, or these genes may be separately contained in different plasmids. For example, the plasmid or plasmids expressing the N gene, the P gene and the L gene of a BDV genome are preferably any of the plasmid or plasmids (1) to (4) described below. The plasmid expressing the G gene of an ABV genome may be one or more plasmids prepared by appropriately introducing the G gene of an ABV genome into one or more of the plasmids (1) to (4) described below, or a separate plasmid expressing the G gene of an ABV genome. The helper plasmid or helper plasmids used in the present invention are preferably a combination of any of the plasmids (1) to (3) with a plasmid expressing the G gene of an ABV genome; or a combination of any of the plasmids (1) to (3) with a plasmid prepared by introducing the G gene of an ABV genome into any of the plasmids (1) to (3).

(1) a plasmid expressing the N gene of a BDV genome, a plasmid expressing the P gene of a BDV genome, and a plasmid expressing the L gene of a BDV genome;
(2) a plasmid expressing the N gene and the P gene of a BDV genome, and a plasmid expressing the L gene of a BDV genome;
(3) a plasmid expressing the N gene and the L gene of a BDV genome, and a plasmid expressing the P gene of a BDV genome; and
(4) a plasmid expressing the N gene, the L gene and the P gene of a BDV genome.

The helper plasmid expressing the M gene of a BDV genome may be a plasmid expressing the M gene of a BDV genome, or a plasmid expressing the M gene of a BDV genome together with one or more genes selected from the group consisting of the N gene, the L gene and the P gene of a BDV genome and the G gene of an ABV genome.

The helper plasmid or helper plasmids provide a viral protein required to replicate the recombinant BDV genome. By introducing the viral vector together with the helper plasmid or helper plasmids into a cell, an infectious recombinant virus can be produced. The viral vector used in the method for preparing the recombinant virus of the present invention and a preferred aspect thereof are the same as those described above.

The helper plasmid or helper plasmids in the present invention may be any plasmid or plasmids that express the N gene, the P gene and the L gene of a BDV genome and the G gene of an ABV genome after introduction in a cell together with the above viral vector. For example, a plasmid expressing the N gene of a BDV genome is preferably a plasmid in which the cDNA of the N gene of a BDV genome is introduced downstream of a promoter sequence. A plasmid expressing the P gene of a BDV genome is preferably a plasmid in which the cDNA of the P gene of a BDV genome is introduced downstream of a promoter sequence. A plasmid expressing the L gene of a BDV genome is preferably a plasmid in which the cDNA of the L gene of BDV is introduced downstream of a promoter sequence. A plasmid expressing the G gene of an ABV genome is preferably a plasmid in which the cDNA of the G gene of an ABV genome is introduced downstream of a promoter sequence. A plasmid expressing the M gene of a BDV genome is preferably a plasmid in which the cDNA of the M gene of a BDV genome is introduced downstream of a promoter sequence. A plasmid expressing two or more genes is preferably a plasmid in which the cDNAs of the desired genes are introduced downstream of a promoter sequence in the desired order.

An envelope protein encoded by an envelope gene is usually a transmembrane protein, and the amino acid sequence of the envelope protein contains a region located outside a cell (extracellular sequence), a transmembrane region (transmembrane sequence), and a region located inside a cell (intracellular sequence). The G gene of an ABV genome in the present invention is preferably the G gene of an ABV genome encoding the intracellular sequence, the transmembrane sequence and the extracellular sequence of the G protein of an ABV genome, but may be the G gene of an ABV genome encoding at least the intracellular sequence of the G protein of an ABV genome. Use of an envelope gene encoding the extracellular sequence and the transmembrane sequence for the helper plasmid or helper plasmids can alter the cell tropism of a virus to be produced according to the viral origin of the envelope gene. Therefore, the helper plasmid expressing the G gene of an ABV genome in the present invention may also express another envelope gene from a different source as long as the effects of the present invention are not impaired. In particular, the helper plasmid expressing the G gene of an ABV genome may include an envelope gene of any enveloped virus that uses host cell membranes to acquire their envelopes, such as vesicular stomatitis virus, rabies virus, measles virus and a retrovirus, or part of the G gene of BDV or Variegated squirrel bornavirus 1 (VSBV-1). For example, when the recombinant virus is used to infect epithelium cells, respiratory cells, or the like, the helper plasmid expressing the G gene of an ABV genome is preferably an envelope gene-expressing helper plasmid encoding the intracellular sequence of the G protein of ABV and encoding the extracellular sequence and the transmembrane sequence of the envelope protein of a virus that has a high tropism for epithelium cells, respiratory cells, or the like (such as, measles virus, Sendai virus, vesicular stomatitis virus, etc).

The cDNA of the N gene of a BDV genome, the cDNA of the P gene of a BDV genome, and the cDNA of the L gene of a BDV genome can be prepared based on the sequence information of the N gene, the P gene and the L gene of a BDV genome, respectively. The cDNA of the G gene of an ABV genome can be prepared based on the sequence information of the G gene of an ABV genome, and based on the sequence information of a known envelope gene. The cDNA of the M gene of a BDV genome can be prepared based on the sequence information of the M gene of a BDV genome. For example, the cDNAs can be prepared from their RNAs using a reverse transcriptase. The cDNAs can also be chemically synthesized using a DNA synthesizer based on their RNA sequences.

The N gene, P gene, L gene and M gene of a BDV genome may be genes having the sequences described in, for example, Cubitt, B., Oldstone, C. and de la Torre, J. C. Sequence and genome organization of Borna disease virus. J. Virol. 68 (3), 1382-1396 (1994), supra. The G gene of an ABV genome may be, for example, a gene having a sequence available from international nucleotide sequence databases under the following accession numbers: PaBV-1: GU249595, PaBV-2: EU781967, PaBV-3: FJ169440, PaBV-4: JN014948, PaBV-7: JX065210, PaBV-5: KR612223, CnBV-1: KC464471, CnBV-2: KC464478, CnBV-3: KC595273, EsBV-1: KF680099, ABBV-1: KF680099, ABBV-2: KJ756399, PaBV-6: FJ794743 or PaBV-8: KJ950625. The above genes may be an RNA synthesized based on the above sequences. A fragment of the genes can be obtained by hybridization and PCR based on the conserved amino acid sequences of the N, P, L and M proteins of a BDV genome or the G protein of an ABV genome. A fragment of the genes can also be obtained by degenerate RT-PCR using a mixed primer designed based on other known sequences of the genes. The nucleotide sequences of the fragments can be determined by a usual method. Part of the nucleotide sequence of each gene in the present invention may be substituted with another nucleotide, deleted, or interrupted by a nucleotide insertion, or some parts of the nucleotide sequence of each gene in the present invention may be transposed, as long as the proteins encoded by the genes retain the original functions. Such derivatives can be also used in the present invention. The above "part" or "parts" may be, for example, in terms of the amino acid residues, one to several (1 to 5, preferably 1 to 3, more preferably 1 or 2) amino acid residues.

The N gene of a BDV genome in the present invention may be, for example, an RNA encoding a polypeptide having at least about 90%, preferably about 95% or more, more preferably about 98% or more sequence identity to the N gene of a BDV genome, and having the functions of the N protein. The P gene of a BDV genome in the present invention may be, for example, an RNA encoding a polypeptide having at least about 90%, preferably about 95% or more, more preferably about 98% or more sequence identity to the P gene of a BDV genome, and having the functions of the P protein. The L gene of a BDV genome in the present invention may be, for example, an RNA encoding a polypeptide having at least about 90%, preferably about 95% or more, more preferably about 98% or more sequence identity to the L gene of a BDV genome, and having the functions of the L protein. The G gene of an ABV genome in the present invention may be, for example, an RNA encoding a polypeptide having at least about 90%, preferably about 95% or more, more preferably about 98% or more sequence identity to the G gene of an ABV genome, and having the functions of the G protein. The M gene of a BDV genome in the present invention may be, for example, an RNA encoding a polypeptide having at least about 90%, preferably about 95% or more, more preferably about 98% or more sequence identity to the M gene of a BDV genome, and having the functions of the M protein. The sequence identity is determined by CLUSTALW, GCG program, GENETYX, or BLAST search.

The envelope gene of a virus other than BDV, such as vesicular stomatitis virus, rabies virus, measles virus and a retrovirus, may be, for example, the gene sequence of vesicular stomatitis virus registered in GenBank under accession No: J02428.1, the gene sequence of rabies virus registered in GenBank under accession No: AB044824.1, etc. Preferred is an envelope gene sequence encoding the extracellular sequence and the transmembrane sequence of such an envelope protein. The envelope gene sequence encoding the extracellular sequence and the transmembrane sequence of such an envelope protein is described in, for example, Garry RF. Proteomics computational analyses suggest that the bornavirus glycoprotein is a class III viral fusion protein (γ penetrene). Virol J. 145(6), Sep. 18, 2009, etc. An RNA synthesized based on the above sequences can also be used as the envelope gene. The envelope gene of a virus in the present invention may be, for example, an RNA encoding a polypeptide having at least about 90%, preferably about 95% or more, more preferably about 98% or more sequence identity to the above envelope gene, and having the functions of the envelope protein.

The helper plasmid or helper plasmids in a linear form may not cause any problems for introduction into cells, but the helper plasmid or helper plasmids are preferably in a circular form. The circular helper plasmid or helper plasmids contain, for example, one or more of the cDNAs of the above proteins and a promoter sequence that are essential for the helper plasmid or helper plasmids of the present invention, and further contain one or more factors that are advantageous for protein expression, including, for example, one or more of nucleic acid sequences encoding an enhancer, an activator (for example, a transactivator), a chaperon, and a processing protease. The helper plasmid or helper plasmids may also contain a factor that is functional in selected cells. The helper plasmid or helper plasmids are preferably constructed using a commercially available plasmid vector capable of replicating itself in cells into which the helper plasmid or helper plasmids are to be introduced. Examples of such a commercially available plasmid vector include pCAGGS, pCXN2, and pCDNA3.1. The promoter sequence contained in the helper plasmid or helper plasmids is preferably an RNA polymerase II promoter.

The helper plasmid or helper plasmids can be prepared by a gene engineering technique known in the art. For example, the plasmid expressing the N gene of a BDV genome, the plasmid expressing the P gene of a BDV genome, and the plasmid expressing the L gene of a BDV genome can be prepared by the method described in 2.2 Plasmid construction in "Materials and methods" in Yanai et al., Microbes and Infection 8 (2006), 1522-1529.

The plasmid expressing two or more genes, for example, the plasmid expressing the N gene and the P gene of a BDV genome can be prepared by, for example, selecting as appropriate a restriction enzyme that does not cleave the cDNA sequence of the N gene or any signal sequences, such as a promoter sequence, from unique restriction enzyme sequence regions downstream of the cDNA sequence of the N gene in a plasmid expressing the N gene of a BDV genome, and inserting the cDNA of the P gene of a BDV genome into the restriction enzyme site for the selected restriction enzyme. The plasmid expressing the N gene and the L gene of a BDV genome can be prepared by, for example, selecting as appropriate a restriction enzyme that does not cleave the cDNA sequence of the N gene or any signal sequences, such as a promoter sequence, from unique restriction enzyme sequence regions downstream of the cDNA sequence of the N gene in a plasmid expressing the N gene of a BDV genome, and inserting the cDNA of the L gene of a BDV genome into the restriction enzyme site for the selected restriction enzyme. A promoter sequence, an internal ribosome entry site, or the like that promotes the expression of the L gene or the P gene can also be inserted into the region between the cDNA region of the N gene and the region into which the cDNA of the L gene or the P gene is inserted.

The plasmid expressing the G gene of an ABV genome can be prepared by, for example, using the cDNA of the G gene of an ABV genome instead of the cDNA of the N gene of a BDV genome in the preparation method for the helper plasmid or helper plasmids expressing the N gene, the L gene and/or the P gene of a BDV genome. The plasmid expressing the M gene of a BDV may be engineered to also express the G gene of an ABV genome, and such a plasmid can be prepared in accordance with, for example, the method described in the instruction manual attached to pEF4/myc-His A, B, and C (Invitrogen).

The helper plasmid expressing an envelope gene encoding the extracellular sequence and the transmembrane sequence of the envelope protein of a virus other than ABV and also encoding the intracellular sequence of the G protein of an ABV genome can be prepared by, for example, PCR using a plasmid expressing the envelope gene of a virus other than ABV as a template with suitable primers to replace the sequence encoding the intracellular sequence of the envelope gene of a virus other than ABV with a sequence encoding the intracellular sequence of the G protein of an ABV genome. Such a helper plasmid can be prepared by, for example, replacing the gene sequence encoding the intracellular sequence of the G protein of BDV with a sequence encoding the intracellular sequence of the G protein of an ABV genome. The gene sequence encoding the intracellular sequence of the G protein of BDV is, for example, positions 3712 to 3747 of the cDNA sequence of the BDV genome of SEQ ID NO: 1 (the nucleotides at positions 3712 to 3747 of SEQ ID NO: 1).

Introduction of the above viral vector into cells can be performed using, for example, a vector composition containing the viral vector. The vector composition may contain the helper plasmid or helper plasmids in addition to the viral vector. The vector composition may contain, in addition to the viral vector and the helper plasmid or helper plasmids, another component such as an appropriate buffer solution, a phosphate buffered saline, and a standard culture broth as appropriate for the introduction method, the subject for introduction, etc.

The amount of the viral vector contained in the vector composition is determined as appropriate for the infection method, the subject for infection, etc., but preferably the vector composition contains, for example, about 0.25 to 2.0 µg/µL of the viral vector in terms of the DNA concentration.

The amount of each helper plasmid contained in the vector composition is preferably, for example, about 0.0125 to 0.125 µg relative to 1 µg of the above viral vector.

The method for introducing the viral vector and the helper plasmid or helper plasmids into cells in vitro is not limited to a particular one, and may be, for example, a known method using a commercially available transfection reagent. Examples of the commercially available transfection reagent include FuGENE (registered trademark) 6 transfection reagent (Roche Molecular Diagnostics, Pleasanton, Calif.), but are not limited thereto. In particular, the viral vector and the helper plasmid or helper plasmids can be introduced into cells by, for example, adding an appropriate amount of a commercially available transfection reagent to a vector composition containing the above amounts of the viral vector and the helper plasmid or helper plasmids, and a buffer solution, and the like, and then adding the resulting mixture to cells, which are usually in an amount of about $1 \times 10^3$ to $1 \times 10^7$ cells, preferably about $1 \times 10^4$ to $1 \times 10^7$ cells relative to 1 µg of the viral vector. The viral vector and the helper plasmid or helper plasmids may be introduced into cells simultaneously or separately. The order for separate introduction is not limited to a particular order.

The cells into which the viral vector is to be introduced may be any mammalian cultured cells that can produce the recombinant virus of the present invention after introduction of the viral vector. Examples of such cells include 293T cells, which are derived from a human kidney, and BHK cells.

The G gene-deficient BDV viral vector is preferably introduced into cells that persistently express the G gene of an ABV genome. Such cells can be prepared by, for example, introducing the desired envelope gene into cells, such as 293T cells and BHK cells, using a given type of plasmid expressing the envelope gene. The plasmid expressing an envelope gene is typically produced by introducing the envelope gene into a given type plasmid in accordance with the method described in the instruction manual attached to the expression plasmid. The helper plasmid expressing the G gene of an ABV genome as described above is also suitable as such a plasmid expressing the envelope gene. The G gene- and M gene-deficient BDV viral vector is preferably introduced into cells that persistently express the M gene of a BDV genome and the G gene of an ABV genome. Such cells can be prepared by, for example, introducing the genes into cells, such as 293T cells and BHK cells, in the same manner as described above.

The cells into which the viral vector has been introduced are cultured to produce a recombinant virus. The culture conditions such as the culture medium to allow for production of a recombinant virus, the culture temperature, and the culture time are determined as appropriate depending on the type of cells. When 293T cells or BHK cells are used, the culture temperature is usually about 36 to 37° C. The culture medium is preferably Dulbecco's Modified Eagle's Medium. The culture time is usually about 24 to 96 hours, preferably about 36 to 48 hours.

The culture of the cells to which the viral vector has been introduced produces a recombinant virus containing the RNA encoded by the viral vector, the N protein, P protein and L protein of a BDV genome and the G protein of an ABV genome. When a helper plasmid expressing the M gene of a BDV genome is further introduced together with the viral vector, the culture of the cells produces a recombinant virus containing the RNA encoded by the viral vector, the N protein, P protein and L protein of a BDV genome, the G protein of an ABV genome and the M gene of a BDV genome.

The production of a recombinant virus in the cells to which the viral vector has been introduced can be confirmed by, for example, recovering the supernatant of the culture medium of the cell culture by centrifugation etc., and using the supernatant to infect cells that a BDV genome can infect, for example, monkey kidney Vero cells, rat glial C6 cells, human glial OL cells, etc. Whether the produced virus is a recombinant virus may be determined by co-culture of the recombinant virus-producing cells with rapidly growing cells as described later, followed by appropriate analysis.

For example, whether the produced virus is a recombinant virus may be determined by quantitative analysis for expression of a foreign gene (for example, GFP etc.) in the infected cells. Whether the produced virus is a persistently infecting virus can be determined by quantitative analysis for expression of a foreign gene (for example, GFP etc.) in the infected cells, followed by analysis of the production of recombinant virus particles of the next generation in the culture supernatant. The production of the recombinant virus particles of the next generation in the culture supernatant can be confirmed by, for example, recovering the supernatant by centrifugation etc., then using the supernatant to infect a different type of cells, and analyzing the expression of a foreign gene from the recombinant virus in the cells.

In the preparation method of the present invention, after the viral vector and the like are introduced into cells to produce a recombinant virus as described above, the step of co-culturing the recombinant virus-producing cells (for example, 293T cells, BHK cells, etc.) with rapidly growing cells is preferably performed to allow for efficient replication of the virus. When the recombinant virus-producing cells are co-cultured with rapidly growing cells, the infectious virus infects the rapidly growing cells. As the rapidly growing cells that are infected with the virus expand in culture, the recombinant virus also replicates itself, and thus the recombinant virus efficiently replicates. The rapidly growing cells are preferably, for example, Vero cells etc. The blending ratio of the rapidly growing cells relative to the recombinant virus-producing cells is, for example, typically about 0.1 to 10 cells, preferably about 0.2 to 2 cells per one recombinant virus-producing cell. The culture conditions for the rapidly growing cells after co-culture are not limited to a particular ones. For example, when Vero cells are used, the cells are cultured in Dulbecco's Modified Eagle's Medium at a culture temperature of usually about 36 to 37° C. for usually about 3 days to 5 weeks, preferably about 3 days to 3 weeks.

When the G gene-deficient BDV viral vector is used, the rapidly growing cells are preferably cells that persistently express an envelope gene from the helper plasmid expressing the G gene of an ABV genome. Such cells can be prepared by, for example, introducing an envelope gene into cells, such as Vero cells, using a plasmid expressing the envelope gene. When the G gene- and M gene-deficient BDV viral vector is used, the rapidly growing cells are preferably cells that persistently express the G gene of an ABV genome and the M gene of a BDV genome. Such cells can be prepared by, for example, introducing the genes into cells, such as Vero cells, using a plasmid or plasmids expressing the genes. Typically, the plasmid or plasmids expressing the genes are easily produced by introducing the desired genes into a given type of plasmid or plasmids according to the instruction manual attached to the expression plasmids. The above-described helper plasmid expressing the G gene of an ABV genome, the above-described helper plasmid expressing the M gene of a BDV genome, or the like may be appropriately used as the plasmid or plasmids for preparation of the rapidly growing cells.

In the preparation method of the present invention, the step of purifying the recombinant virus is preferably performed after the production (and replication) of the recombinant virus in cells. The purification can be performed by a known method, and the purification method is not limited to a particular one and can be selected as appropriate for the subject for infection.

Infection of cultured cells with the recombinant virus can be performed by, for example, producing (and replicating) the recombinant virus as described above, then recovering the supernatant of the cultured cells that have produced the recombinant virus, and disrupting the cells. The disruption of the cells can be performed by, for example, freezing and thawing, or using an ultrasonic homogenizer. The disrupted cell debris is then removed from the disrupted cell solution. The removal of the disrupted cell debris from the disrupted cell solution can be performed by centrifugation (for example, at 4° C., 800 g for 10 minutes) etc. After removal of the disrupted cell debris, the resulting solution is filtrated through a filter membrane with a pore size of 0.22 μm or 0.45 μm to give a supernatant containing the recombinant virus. This supernatant can be used to allow the recombinant virus to infect cultured cells. The supernatant containing the recombinant virus can also be used after concentration by a known method.

When the recombinant virus is used to infect cells in a living body (cells in an animal individual), the supernatant containing the recombinant virus is preferably highly purified by concentration gradient ultracentrifugation with an ultracentrifuge to give virus particles. The purified virus particles are suspended in, for example, a phosphate buffered saline and diluted, and a suitable amount of the virus particles is used to infect an animal.

4. Introduction Method of Foreign Gene The foreign gene integrated into the above recombinant virus can be introduced into cells or a living body using the virus to infect the cells. Such a method for introducing a foreign gene, involving the step of infecting in vitro cells or an animal with the above recombinant virus or a recombinant virus prepared by the above method, is also one aspect of the present invention.

The animal to be infected with the recombinant virus is not limited, and examples thereof include mammals, birds, reptiles, and amphibians. Preferred are mammals, such as humans, monkeys, horses, dogs, cats, pigs, sheep, goats, rats, mice, rabbits, and cattle; more preferred are rats, mice, or humans; and further preferred are mice or humans. The cells of such an animal are preferred as cells to be infected with the recombinant virus. Since BDV is a neurotropic virus, the cells to be infected therewith are preferably mammalian nerve cells, and more preferably cranial nerve cells. Preferred are rat, mouse, or human nerve cells. The cells may be cultured cells or cells in a living body. Examples of the mammalian cranial nerve cells include glia cells, nerve cells of the cerebral cortex, hippocampal nerve cells, cerebellar nerve cells, and mesencephalic nerve cells. Preferred cultured mammalian cranial nerve cells are OL cells, C6 cells, U373 cells, N2a cells, N18 cells, PC12 cells, and SK-N-SH cells.

The recombinant virus produced from the G gene-deficient BDV viral vector and the helper plasmid expressing the G gene of an ABV genome together with an envelope gene of another virus displays infectious tropism depending on the viral origin of the envelope gene. For example, when the envelope gene of a virus other than ABV (preferably an envelope gene encoding the extracellular sequence and the transmembrane sequence of the envelope protein of a virus other than ABV and also encoding the intracellular sequence of the G protein of an ABV genome) is used to produce the helper plasmid, the resulting recombinant virus is suitable for use in infection of cells for which the virus displays infectious tropism.

When the recombinant virus of the present invention is used to infect cells in vitro, for example, cultured cells, a viral solution diluted in a culture medium such as Dulbecco's Modified Eagle's Medium or a phosphate buffered saline is preferably prepared by serially diluting the supernatant containing the recombinant virus obtained by the above purification method. The concentration of the recombinant virus in the diluted viral solution is determined as appropriate depending on the type of cells to be infected with the virus, etc. For example, when mammalian nerve cells or the like are used, the concentration is usually about 0.01 to 10 MOI (multiplicity of infection; infectivity titer) (the amount means that there exist 0.01 to 10 infectious virus particles per cell), preferably about 1 to 10 MOI. The diluted viral solution is used to infect cells with the recombinant virus.

When the recombinant virus is used to infect cells in a living body (an animal), preferably, highly purified virus particles as described above are suspend in, for example, a phosphate buffered saline and diluted with a phosphate buffered saline, and a suitable amount of the virus particles is used to infect an animal. The concentration of the recombinant virus in the diluted viral solution is determined as appropriate depending on the subject for infection. For example, when the subject for infection is mammalian nerve cells, the subject is preferably inoculated with the diluted recombinant virus solution having a virus titer of about $1\times10^{-1}$ to $1\times10^{9}$ FFU (focus-forming unit). When a mouse or a rat is inoculated with the diluted recombinant virus solution, preferably the virus titer of the diluted solution is typically about $1\times10^{-1}$ to $1\times10^{7}$ FFU. When a dog, a cat, or a human is inoculated with the diluted recombinant virus solution, preferably the virus titer is typically about 10 to $1\times10^{8}$ FFU. When a horse or cattle is inoculated with the diluted recombinant virus solution, preferably the virus titer is typically about $1\times10^{3}$ to $1\times10^{12}$ FFU. When a human is inoculated with the diluted recombinant virus solution, preferably the virus titer is typically about $1\times10^{3}$ to $1\times10^{9}$ FFU. The foreign gene introducing agent described later is also suitable for infection of cells in a living body with the recombinant virus.

For example, when mammalian cranial nerve cells are infected with the recombinant virus, the diluted recombinant virus solution is preferably administered to the nasal cavity of a mammal. When the cranial nerve cells of a mouse, a rat, or the like are infected with the recombinant virus in an animal experiment, the diluted recombinant virus solution can be administered directly to the brain of the animal.

The inoculum dose of the recombinant virus is typically about 5 μL to 1 mL of the diluted solution containing the above concentration of the recombinant virus per dose for intranasal inoculation, and typically about 1 to 50 μL per dose for intracerebral inoculation. The inoculum dose of the recombinant virus in an animal is determined as appropriate for the weight etc. of the animal. For example, when a mouse or a rat is intranasally inoculated with the diluted solution containing the above concentration of the recombinant virus, the inoculum dose is typically about 5 to 200 μL per dose, preferably about 10 to 100 μL per dose.

When cells other than cranial nerve cells in a living body are infected with the recombinant virus, the diluted recombinant virus solution is preferably administered parenterally. For example, a mammal is preferably inoculated with the diluted recombinant virus solution via intraperitoneal route, intravascular route, intramuscular route, or the like.

The inoculum dose of the recombinant virus is determined as appropriate for the inoculation site or the like and is not limited to a particular dose. For example, when the virus titer of the diluted recombinant virus solution is about $1\times10^{-1}$ to $1\times10^{9}$ FFU, the inoculum dose of the diluted recombinant virus solution for a mouse is typically about 5 to 500 μL, preferably about 20 to 200 μL per dose.

5. Foreign Gene Introducing Agent

A foreign gene introducing agent containing (1) the above viral vector, (3) the above recombinant virus, or a recombinant virus prepared by the above method is also one aspect of the present invention. In a preferred aspect, the foreign gene introducing agent contains the above recombinant virus or a recombinant virus prepared by the above method. Such a foreign gene introducing agent is suitable for infection of in vitro cells or cells in a living body (an animal) with the recombinant virus in the above introduction method of a foreign gene. This aspect of the present invention is suitable for introduction of a foreign gene into nerve cells etc. of an animal. In particular, this aspect of the present invention is suitable for introduction of a foreign gene into cranial nerve cells.

In a preferred aspect of the foreign gene introducing agent of the present invention, the foreign gene introducing agent containing the above recombinant virus or a recombinant virus prepared by the above method is used for cranial nerve cells. Preferred cranial nerve cells are mammalian cranial nerve cells, including glia cells, nerve cells of the cerebral cortex, hippocampal nerve cells, cerebellar nerve cells, and mesencephalic nerve cells. The foreign gene introducing agent of the present invention may further contain another drug such as a therapeutic agent for neurological diseases, and may also contain a pharmaceutically acceptable component depending on the dosage form. The dosage form of the foreign gene introducing agent of the present invention is preferably a dosage form for parenteral administration, for example, an injection, an infusion, an ointment, a gel, a cream, a patch, a nebula, a spray, or the like. Preferred is an injection.

An injection for parenteral administration may be an aqueous injection or an oily injection. When the injection is an aqueous injection, it can be prepared according to a known method by, for example, adding the recombinant virus to a solution containing a pharmaceutically acceptable additive as appropriate in an aqueous solvent (water for injection, purified water, or the like), then sterilizing the mixture by filtration through a filter or the like, and packing the resulting solution into a sterilized container. Examples of the pharmaceutically acceptable additive include isotonizing agents such as sodium chloride, potassium chloride, glycerin, mannitol, sorbitol, boric acid, borax, glucose, and propylene glycol; buffers such as phosphate buffer solution, acetate buffer solution, borate buffer solution, carbonate buffer solution, citrate buffer solution, Tris buffer, glutamate buffer solution, and epsilon aminocaproic acid buffer solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid, and borax; thickeners such as hydroxyethyl cellulose, hydroxypropyl cellulose, polyvinyl alcohol, and polyethylene glycol; stabilizers such as sodium hydrogen sulfite, sodium thiosulfate, sodium edetate, sodium citrate, ascorbic acid, and dibutylhydroxytoluene; and pH adjusters such as hydrochloric acid, sodium hydroxide, phosphoric acid, and acetic acid. A suitable solubilizer may be further added to the injection, and examples of the solubilizer include alcohols such as ethanol; polyalcohols such as propylene glycol and polyethylene glycol; and nonionic surfactants such as polysorbate 80, polyoxyethylene hydrogenated castor oil 50, lysolecithin, and Pluronic polyol. The injection may also contain proteins such as bovine serum albumin and keyhole limpet hemocyanin; polysaccharides such as aminodextran; and the like. When the injection is an oily injection, for example, sesame oil or soybean oil is used as an oily solvent, and benzyl benzoate or benzyl alcohol may be mixed as a solubilizer. A prepared injection solution is typically packed into a suitable ampule, vial, or the like. A liquid preparation such as an injection can be subjected to cryopreservation, lyophilization, or the like, which removes the water in the preparation, and then stored. Before use, the lyophilized preparation is redissolved by addition of water for injection or the like.

The amount of the recombinant virus contained in the foreign gene introducing agent of the present invention varies depending on the dosage form or the administration route of the foreign gene introducing agent, but the amount is usually selected and determined as appropriate from the range of about 0.0001 to 100 w/v % in a final preparation. The administration method and administration amount of the foreign gene introducing agent are the same as those of the recombinant virus in the above method for introducing a foreign gene. The foreign gene introducing agent of the present invention is useful as, for example, a composition for gene delivery for treatment of brain and neurological diseases or chronic liver diseases, such as hepatitis C, of an animal, or for anti-tumor therapy, vaccination, etc. The subject of administration of the foreign gene introducing agent of the present invention is preferably the mammals as described above.

6. Use of Viral Vector

The viral vector, the recombinant virus, the method for introducing a foreign gene, and the foreign gene introducing agent of the present invention can be applied to various fields as a gene introduction technique that does not affect a host chromosome.

For example, the viral vector and the recombinant virus of the present invention can be used as a gene delivery vector for treatment of brain and neurological diseases of an animal including humans. The viral vector and the recombinant virus can also suitable for vaccination against chronic liver diseases, tumors, infections, etc.

Examples of the brain and neurological diseases include Alzheimer's disease, Parkinson's disease, multiple sclerosis, schizophrenia, autism, and other psychiatric functional disorders. The recombinant virus of the present invention is useful for treatment or prevention of such diseases. For example, when a gene encoding an enzyme that degrades a protein that causes brain and neurological diseases or a gene encoding a nucleic acid sequence having a function of inhibiting the expression of the causal protein, or the like is inserted into the viral vector of the present invention as a foreign gene, a recombinant virus produced from the viral vector infects cranial nerve cells to cause degradation of the causal protein or suppression of the expression of the causal protein, thereby preventing or treating the disease. For prevention or treatment of a disease caused by reduced secretion of a brain substance (for example, serotonin, dopamine, somatostatin, neprilysin, or the like), a gene encoding such a brain substance is inserted into the viral vector, and a recombinant virus produced from the viral vector is used to infect cranial nerve cells to allow production of the brain substance, thereby preventing or treating the brain disease.

The term "treatment" means complete cure of a clinical condition, or inhibition of the progress and/or deterioration of the symptoms to prevent the progress of the clinical condition even when the disease is not cured completely, or improvement of the whole or part of a clinical condition to lead to recovery. The term "prevention" means prevention, inhibition or delay of the onset of a clinical condition.

The viral vector and the recombinant virus of the present invention can also be used to treat or prevent viral encephalitis including Japanese encephalitis. The viral vector and the recombinant virus of the present invention are also suitable for use in brain and neurological diseases in experimental animals, companion animals or food-producing animals. Examples of brain and neurological diseases include BSE (bovine spongiform encephalopathy) and rabies. Examples of the experimental animals include mice, rats, guinea pigs, rabbits, cats and dogs. Examples of the companion animals include mice, rats, guinea pigs, rabbits, cats and dogs. Examples of the food-producing animals include cattle, horses, pigs and sheep.

The viral vector and the recombinant virus of the present invention can also be used for visualization techniques of nerve cells in the field of neuroscience. The viral vector of the present invention is also useful as an RNA viral vector expressing a functional RNA molecule, and can be used for a technique for stably expressing a functional RNA such as an siRNA, a miRNA, and an RNA aptamer in a vector. For example, when a sequence encoding a functional RNA such as an siRNA, a miRNA, and an RNA aptamer is inserted into the viral vector of the present invention as a foreign gene, the functional RNA molecule can be expressed in the desired cells. The viral vector and the recombinant virus of the present invention can also be used to express a single chain antibody (scFv) in the brain.

The viral vector or the recombinant virus of the present invention can be modified to specifically infect tumor cells by using an envelope protein derived from another virus. Such a viral vector or a recombinant virus can serve as an antitumor viral vector that introduces a drug gene or an siRNA inhibiting overexpressed gene into tumor cells. Further, when a gene having a neutralization activity against HIV, influenza virus, or the like (for example, env, gag, etc. of HIV; the HA gene, the NA gene, etc. of influenza virus; etc.) is introduced as a foreign gene, the viral vector or the recombinant virus of the present invention can be used as a recombinant vaccine. For infections that can take a chronic course, such as HCV, the viral vector or the recombinant virus containing an siRNA against a target virus genome is beneficial for the development of a novel infection therapy using a functional RNA.

The viral vector and the recombinant virus of the present invention can be used to infect stem cells of various origins, pluripotent stem cells such as iPS cells, or cancer stem cells to produce a safe cell population that can be used for therapy of the diseases as described above.

A kit for introducing a foreign gene, the kit comprising the above viral vector, is also one aspect of the present invention.

The kit of the present invention comprising the viral vector may further contain as appropriate a helper plasmid, cells into which a foreign gene is to be introduced, a buffer solution, a culture medium, and the like. A preferred aspect of the viral vector is as described above. The cells into which a foreign gene is to be introduced are preferably nerve cells, such as cranial nerve cells. The kit of the present invention is suitable for introduction of a foreign gene into cranial nerve cells etc., which introduction is technically difficult.

EXAMPLES

The present invention will be described in detail below with reference to Examples. These Examples are provided for illustrating purposes only and should not be construed as limiting the scope of the present invention.

Example 1

1. Preparation of Plasmid pCAG-Fct

A plasmid was constructed based on the plasmid pCAG-HR-SV3 described in Yanai et al., Microbes and Infection 8 (2006), 1522-1529 by replacing the region of the chloramphenicol acetyltransferase (CAT) gene inserted in the plasmid with the genome sequence of the Borna disease virus strain He/80 (SEQ ID NO: 1).

A cytomegalovirus (CMV)-derived BDV mini genome vector (pCMV-HR) was produced as follows. A chemically synthesized oligonucleotide encoding a hammer head ribozyme (HamRz) (Briese et al., Proc. Natl. Acad. Sci. U.S.A 89 (1992) 11486-11489; and Le Mercier et al., J. Virol., 76 (2002) 2024-2027) was annealed with a chemically synthesized oligonucleotide encoding the 5' untranslated region (UTR) sequence of BDV (Cubitt, B., Oldstone, C. and de la Torre, J. C., Sequence and genome organization of Borna disease virus. J. Virol. 68 (3), 1382-1396 (1994)) and ligated between the KpnI and XhoI sites of the vector pcDNA3 (Invitrogen, San Diego, Calif.). The obtained plasmid was cleaved at the Eco47III and XbaI sites. A BDV 3' UTR fused to a hepatitis δ virus ribozyme (HdRz) and a cDNA clone encoding the BDV strain He/80 genome were inserted into the plasmid to give the plasmid pc-HR. The BDV 3' UTR fused to HdRz was prepared by amplified it from the plasmid phuPol I-MG (Perez et al., J. Gen. Virol. 84 (2003) 3099-3104). Finally, the BglII and XbaI fragment of the pc-HR was inserted between the BamHI and XbaI sites of pBluescript SKII (−) (Stratagene, La Jolla, Calif.) to give the pCMV-HR.

The BDV mini genome vector pCAG-HR containing CAG (a complex of a chicken β-actin promoter and a CMV enhancer) was produced as follows. A CAG promoter was first subcloned into pBluescript SKII (−) (Stratagene, La Jolla, Calif.) (pBS-CAG). The CAG promoter is a hybrid promoter composed of a cytomegalovirus IE enhancer fused to a chicken β-actin promoter, and is described in Sawichi et al., Exp. Cell Res. 244 (1998) 367-369. Then, the region from HamRz to HdRz in the pCMV-HR was amplified by PCR, and the PCR product was inserted between the blunt ends at the SalI and EcoRI sites in the pBS-CAG.

A fragment of 113 nucleotides at the 5' end of an SV40 origin/promoter (SV3 region) was amplified from pEGFP-N1 (Clontech) by PCR (Clontech Laboratory, Inc., Palo Alto, Calif.). The PCR product was inserted into the NotI site of the pCAG-HR to give the plasmid pCAG-Fct.

2. Preparation of BDV Genome Plasmid Having GFP Inserted into Untranslated Region Between P Gene and M Gene (pCAG-Fct-P/M-GFP)

The plasmid pCAG-Fct-P/M was prepared by inserting an insertion cassette for a foreign gene into the untranslated region between the P gene and the M gene as follows.

A) The pCAG-Fct (a plasmid in which the cDNA of the Borna virus strain He/80 (SEQ ID NO: 1) was cloned) prepared in the above section 1 was used as a template, and the region between the EcoT22I site and the Bst1107I site was amplified by two separate PCRs using primers 1 and 4, and primers 2 and 3, respectively. Then, 0.5 μL of each of the PCR products were mixed together and amplified again using primers 1 and 2 to give an insertion cassette for a foreign gene, which cassette harbors the BstBI and PacI sites between the P gene and the M gene.

B) The PCR product of A) was integrated into the pCAG-Fct using EcoT22I and Bst1107I to give pCAG-Fct-P/M.

C) GFP was then inserted using BstBI and PacI to give the plasmid pCAG-Fct-P/M-GFP.

```
Primers
Primer 1:
                                    (SEQ ID NO: 5)
5-GGAATGCATTGACCCAACCGGTAGACCAGC-3

Primer 2:
                                    (SEQ ID NO: 6)
5-AACATGTATTTCCTAATCGGGTCCTTGTATACGG-3

Primer 3:
                                    (SEQ ID NO: 7)
5-ttcgaaGGTTGGttaattaaccataaaaaaatcgaatcacc-3

Primer 4:
                                    (SEQ ID NO: 8)
5-ttaattaaCCAACCttcgaaGGTGATTCGATTTTTTTATGG-3
```

3. Preparation of G-Gene Deficient BDV Genome Plasmid (p/mGFP ΔG LL)

Figure 6:
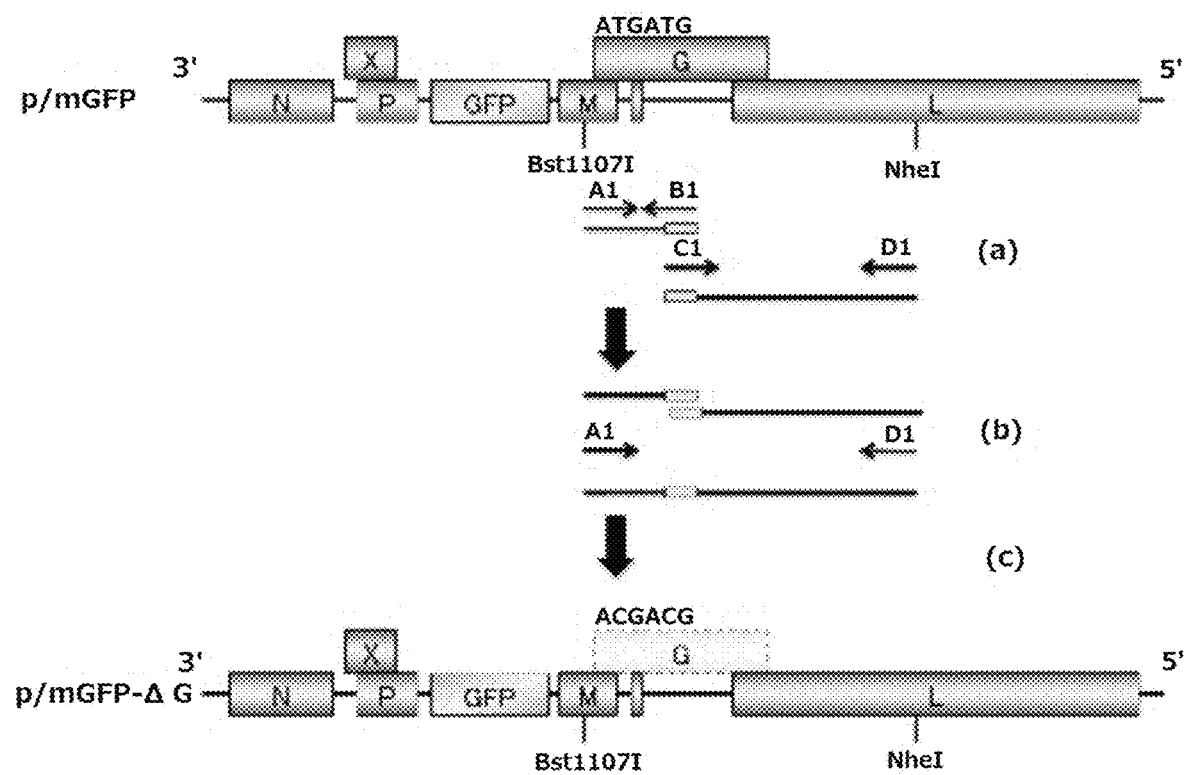
FIG. 6 is a schematic view of the preparation procedure of a plasmid p/mGFP ΔG.

Point mutations were introduced into the pCAG-Fct-P/M-GFP prepared as above by PCR to delete the G gene encoding the viral membrane glycoprotein. Specifically, two sequences encoding methionine in the G gene (positions 2236 to 2238 and 2248 to 2250 in the genome (i.e., the nucleotide sequence of SEQ ID NO: 1)) were replaced with sequences encoding threonine (ATG→ACG). FIG. 6 shows a schematic view of the preparation procedure of the plasmid p/mGFP ΔG encoding the G-gene deficient BDV virus. Two separate PCRs (25 cycles of 98° C. for 10 seconds, 55° C. for 5 seconds, and 72° C. for 0.5 or 1 minute) were performed using the p/mGFP as a template using primers A1 and B1, and primers C1 and D1, respectively, whose sequences are shown in Table 1 ((a) in FIG. 6).

PCR (25 cycles of 98° C. for 10 seconds, 55° C. for 5 seconds, and 72° C. for 1.5 minutes) was performed again using the both amplification products (the 1st PCR products) as templates using the above primers A1 and D1 ((b) in FIG. 6). The resulting amplification product (the 2nd PCR product), in which methionine in the G gene was mutated into threonine, was integrated into the vector p/mGFP using restriction enzymes Bst1107I and NheI to give p/mGFP ΔG ((c) in FIG. 6).

Figure 7:
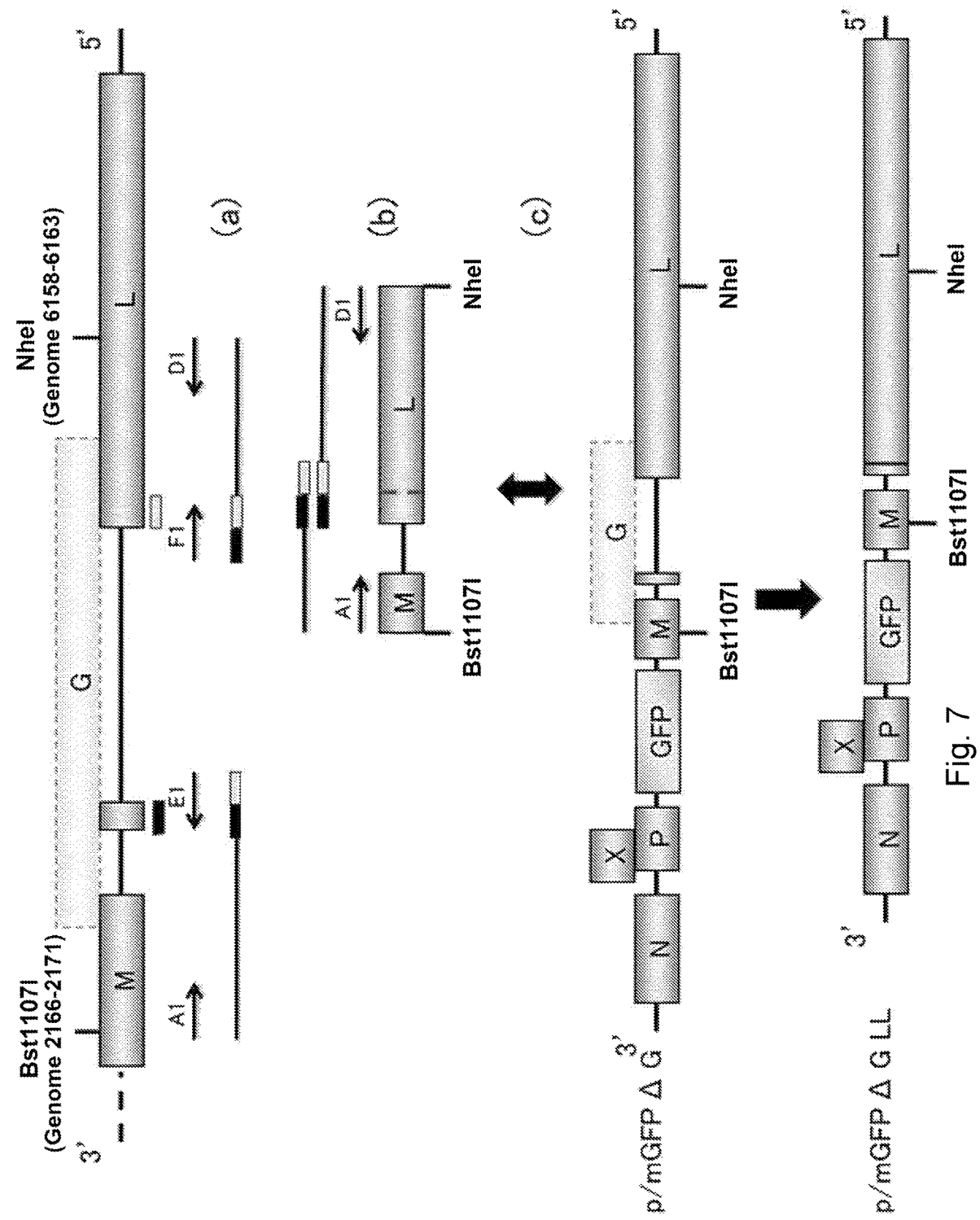
FIG. 7 is a schematic view of the preparation procedure of a plasmid p/mGFP ΔG LL.

Then, the intron region of the L gene (part of the region of the G gene), which became unnecessary, was deleted and the exons of the L gene were spliced together (L linearize). Specifically, the region from the restriction enzyme site Bst1107I (positions 2166 to 2171 in the nucleotide sequence of SEQ ID NO: 1) to the first half of the exon of the L gene and the region of the latter half of the exon of the L gene (until the NheI site (positions 6158 to 6163 in the nucleotide sequence of SEQ ID NO: 1)) were separately amplified, spliced together, and introduced into the p/mGFP ΔG. The outline of this procedure is shown in FIG. 7. First, two separate PCRs (25 cycles of 98° C. for 10 seconds, 55° C. for 5 seconds, and 72° C. for 0.5 minutes) were performed using the p/mGFP ΔG as a template using primers A1 and E1, and primers F1 and D1, respectively, whose sequences are shown in Table 1 ((a) in FIG. 7). Then, PCR (25 cycles of 98° C. for 10 seconds, 55° C. for 5 seconds, and 72° C. for 1 minute) was performed using the both amplification products (the 1st PCR products) as templates using the above primers A1 and D1 ((b) in FIG. 7). The resulting amplification product (the 2nd PCR product), in which the intron region of the L gene was deleted, was integrated into the vector p/mGFP ΔG using restriction enzymes Bst1107I and NheI to give p/mGFP ΔG LL ((c) in FIG. 7).

TABLE 1

| Primer No. | Sequence |
|---|---|
| A1 | CCGTATACAAGGACCCGATTAGGAAATACATGTT (SEQ ID NO: 10) |
| B1 | AAGAGAAGACGTTGAAAGCTGCGTTAATTGCG (SEQ ID NO: 11) |
| C1 | CGCAATTAACGCAGCTTTCAACGTCTTCTCTT (SEQ ID NO: 12) |
| D1 | GGGTCTGCAAGAGTGCTAGCTGAAAGGGC (SEQ ID NO: 13) |
| E1 | GCGAAGGAGGCTCGCATGAAATGACATTTTCCG (SEQ ID NO: 14) |
| F1 | TCATTTCATGCGAGCCTCCTTCGCGAGGAGGAGAC (SEQ ID NO: 15) |

4. Preparation of BDV Genome Plasmid (p/m PaBV4G GFP ΔG LL) in which G Gene of ABV was Inserted S3 and T2 sequences and Sse8387I, AscI, AsiSI and SwaI sites as an insertion cassette for a foreign gene were inserted between the P gene and the GFP gene in the p/mGFP ΔG LL produced as above to give p/m tandem GFP ΔG LL.

S3:
(SEQ ID NO: 16)
5-TAAAAAAATCGAATCA-3

T2:
(SEQ ID NO: 17)
5-TAAAAAAA-3

The cDNA of the G gene of PaBV-4 was inserted into the insertion cassette of the p/m tandem GFP ΔG LL to give p/m PaBV4G GFP ΔG LL. Briefly, PCR (30 cycles of 98° C. for 10 seconds, 55° C. for 5 seconds and 72° C. for 10 seconds) was performed using the cDNA of the G gene of PaBV-4 as a template using primers 5 and 6. The PCR product was integrated into the p/m tandem GFP ΔG LL using AscI and AsiSI to give p/m PaBV4G GFP ΔG LL (FIG. 3A).

Primer 5:
(SEQ ID NO: 18)
5'-AAAGGCGCGCCATGCTGCATTCAACGTATTCTCGTT-3'

Primer 6:
(SEQ ID NO: 19)
5'-AAAGCGATCGCTTATTCCGACCACCTTCCGAG-3'

5. Preparation of Helper Plasmids

Helper plasmids, i.e., a plasmid expressing the N gene of a BDV genome (pcN), a plasmid expressing the P gene of a BDV genome (pCXN2-P), and a plasmid expressing the L gene of a BDV genome (pcL) were prepared by the following procedures.

The pcN was prepared by amplifying the N gene region from a pHA-p40N plasmid (Kobayashi T, Watanabe M, Kamitani W, Zhang G, Tomonaga K and Ikuta K. Borna disease virus nucleoprotein requires both nuclear localization and export activities for viral nucleocytoplasmic shuttling. J. Virol. 75: 3404-3412. (2001)) by PCR, and inserting the PCR product into the pBS-CAG as described above.

The plasmid pCXN2-P was prepared by inserting a fragment obtained by gel extraction from pcD-P (Zhang G, Kobayashi T, Kamitani W, Komoto S, Yamashita M, Baba S, Yanai H, Ikuta K and Tomonaga K. Borna disease virus phosphoprotein represses p53-mediated transcriptional activity by interference with HMGB1. J. Virol. 77: 12243-12251. (2003)) between the EcoRI and XhoI sites of pCXN2 (Niwa H, Yamamura K, Miyazaki J 1991 Efficient selection for high-expression transfectants with a novel eukaryotic vector. Gene 108: 193-199).

The pcL was prepared by the method described in Perez et al., J. Gen. Virol. 84 (2003) 3099-3104. The nucleotide sequences of the recombinant plasmids were determined by DNA sequencing.

6. Preparation of Recombinant Virus

The p/m PaBV4G GFP ΔG LL and the helper plasmids (the N gene expression plasmid, the P gene expression plasmid, and the L gene expression plasmid; called pcN, pCXN2-P and pcL, respectively) were introduced into 293T cells using FuGENE (registered trademark) 6 transfection reagent (Roche Molecular Diagnostics, Pleasanton, Calif.) or Lipofectamine (registered trademark) 2000 (Invitrogen). The viral vector p/m PaBV4G GFP ΔG LL in a volume of 1 to 4 µg was added to $1 \times 10^4$ to $1 \times 10^6$ cells (293T cells). The helper plasmids were added in the following volumes: 0.125 to 0.5 µg of the pcN, 0.0125 to 0.05 µg of the pCXN2-P, and 0.125 to 0.5 µg of the pcL.

The viral vector and the helper plasmids were introduced into 293T cells using Lipofectamine (registered trademark) 2000 (Invitrogen). After the introduction of the genes, the cells were cultured at 37° C., and passaged three days after the introduction, and co-cultured with Vero cells. The co-cultured Vero cells were recovered as Vero cells infected with a chimeric virus expressing PaBV-4G.

At 48 hours or more post-infection to the cultured cells, the spread of infection in the cells and the release of the virus to the supernatant of the infected cells were evaluated by indirect immunofluorescence antibody assay and western blotting, and the virus titer in the supernatant was measured by infecting the recombinant virus to Vero cells. The results indicated that the virus production begun to be observed 24 hours after the infection.

Example 2

Recovery of Pseudovirus

G gene-deficient recombinant BDV cells were prepared using the p/mGFP ΔG LL and the helper plasmids (the N gene expression plasmid, the P gene expression plasmid, and the L gene expression plasmid; called pcN, pCXN2-P and pcL, respectively) in the same manner as in Example 1. The cells were seeded on a 10 cm petri dish (3.0×10$^6$ cells), and 10 µg of each of the G Protein expression plasmids was introduced using TransIT (registered trademark)-293 (Ta-KaRa). The G protein expression plasmids expressed the G protein of Variegated squirrel bornavirus (VSBV), Parrot bornavirus 4 (PaBV-4), Parrot bornavirus 5 (PaBV-5), or Munia bornavirus 1 (MuBV-1). The cells to which each plasmid was separately introduced were cultured in Dulbecco's modified Eagle's medium (DMEM) supplemented with 10% fetal bovine serum (FCS) at 37° C. After 48 hours, the cells were washed twice with DMEM, 1.2 mL of DMEM was added, and the petri dish was stored at −80° C. for 1 hour. Freezing at −80° C. and thawing at room temperature were repeated twice, and the medium in the petri dish was recovered. The recovered medium was centrifuged at 4° C., 3,000 rpm for 5 minutes, and the supernatant was used as a pseudovirus solution.

Figure 8:
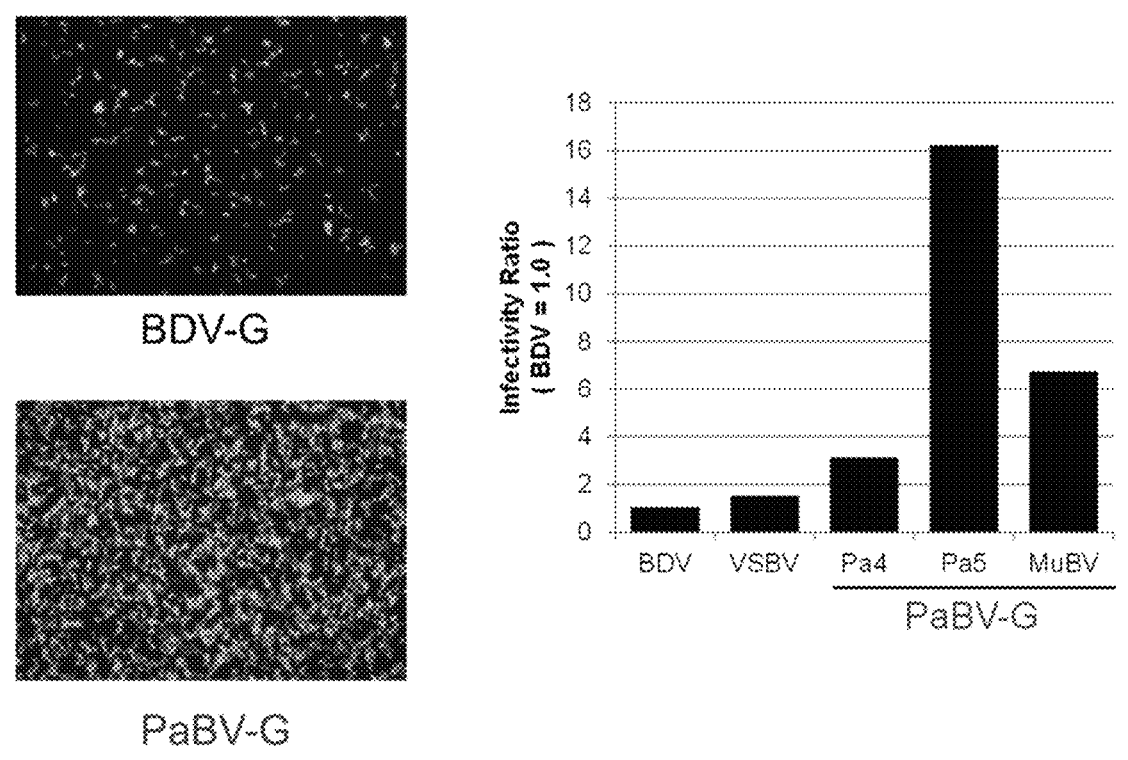

The pseudovirus recovered as above was used to inoculate Vero cells. The left panels in FIG. 8 are images taken under a fluorescent microscope four days after the inoculation of the Vero cells. The right panel in FIG. 8 is a chart showing the number of the GFP-positive cells (relative value) in the same experiment.

INDUSTRIAL APPLICABILITY

A recombinant virus produced from the viral vector of the present invention is capable of efficiently expressing a foreign gene in a cell nucleus with no cytotoxicity, and is a safe vector that is not integrated into a host chromosome because the virus genome is composed of RNA. The viral vector of the present invention utilizes a Borna disease virus, which displays tropism for nerve cells, and therefore the viral vector functions as a highly specific vector capable of preferentially introducing a foreign gene into the central nervous system. Due to these advantages, the present invention is very useful and can be used as a gene introduction technique that does not affect a host chromosome and can be applied to various fields, such as the treatment and prevention of brain and neurological diseases, visualization techniques of nerve cells in the field of neuroscience, etc. The present invention can also be applied to a technique to allow a vector to stably express a functional RNA such as an siRNA, a miRNA and an RNA aptamer. Therefore, the present invention is useful in the various fields, such as medical care, animal medical care, clinical trials, and research.

The invention claimed is:

1. A viral vector comprising a cDNA from a recombinant viral RNA having a sequence of a Borna disease viral genome comprising a disrupted G gene of from a Borna disease viral genome and an inserted G gene from an avian bornaviral genome.

2. The viral vector according to claim 1, which comprises:
(a) the cDNA of a recombinant viral RNA having a sequence from a Borna disease viral genome comprising a disrupted G gene from the Borna disease viral genome and an inserted G gene from an avian bornaviral genome, wherein the cDNA of the recombinant viral RNA has at least an N gene, an X gene, a P gene and an L gene of the Borna disease viral genome in the same order as in the Borna disease viral genome and an inserted foreign gene;
(b) DNAs encoding ribozymes; and
(c) a promoter sequence,
wherein (b) the DNAs encoding ribozymes are located upstream and downstream of (a) the cDNA of the recombinant viral RNA, and (a) the cDNA of the recombinant viral RNA and (b) the DNAs encoding ribozymes are located downstream of (c) the promoter sequence.

3. The viral vector according to claim 2, wherein (a) the cDNA of the recombinant viral RNA further comprises a disrupted M gene of the Borna disease viral genome.

4. The viral vector according to claim 2, wherein (a) the cDNA of the recombinant viral RNA has the foreign gene inserted in an untranslated region between open reading frames of the P gene and the M gene of the Borna disease viral genome.

5. The viral vector according to claim 2, wherein (c) the promoter sequence is an RNA polymerase II promoter sequence.

6. The viral vector according to claim 2, wherein (b1) a cDNA encoding a hammer head ribozyme is located upstream of (a) the cDNA of the recombinant viral RNA, and (b2) a cDNA sequence encoding a hepatitis δ virus ribozyme is located downstream of (a) the cDNA of the recombinant viral RNA.

7. The viral vector according to claim 2, wherein (a) the cDNA of the recombinant viral RNA comprises:
restriction enzyme sites at the 3' and 5' ends of the foreign gene;
a sequence of SEQ ID NO: 9 located between the restriction enzyme site at the 3' end of the foreign gene and the open reading frame of the P gene and a sequence of SEQ ID NO: 9 located between the restriction enzyme site at the 5' end of the foreign gene and the open reading frame of the L gene, or
when the cDNA of the recombinant viral RNA has the M gene of the Borna disease viral genome in the same location as in the Borna disease viral genome, a sequence of SEQ ID NO: 9 located between the restriction enzyme site at the 3' end of the foreign gene and the open reading frame of the P gene and a sequence of SEQ ID NO: 9 located between the restriction enzyme site at the 5' end of the foreign gene and the open reading frame of the M gene;
at least an inserted nucleotide sequence cc between the restriction enzyme site at the 3' end of the foreign gene and the sequence of SEQ ID NO: 9 located near the 3' end of the foreign gene; and
at least an inserted nucleotide sequence cca between the restriction enzyme site at the 5' end of the foreign gene and the sequence of SEQ ID NO: 9 located near the 5' end of the foreign gene.

8. A recombinant virus comprising an RNA encoded by the viral vector according to claim 1.

9. A method for preparing a recombinant virus, the method comprising:
introducing into a cell in vitro the viral vector according to claim 1 together with (i) a plasmid or plasmids expressing an N gene, a P gene and an L gene of a Borna disease viral genome and a G gene of an avian bornaviral genome or (ii) a plasmid or plasmids expressing an N gene, a P gene and an L gene of a Borna disease viral genome and a plasmid expressing a G gene of an avian bornaviral genome, as a helper plasmid or helper plasmids, and
culturing the cell having the viral vector and the helper plasmid or helper plasmids introduced therein to produce a recombinant virus.

10. The method for preparing a recombinant virus according to claim 9, further comprising introducing a plasmid expressing an M gene of a Borna disease viral genome as a helper plasmid into the cell in vitro.

11. A method for introducing a foreign gene, the method comprising infecting a cell or an animal with the recombinant virus according to claim 8.

12. The method for introducing a foreign gene according to claim 11, further comprising introducing a foreign gene into cranial nerve cells.

* * * * *

UNITED STATES PATENT AND TRADEMARK OFFICE
CERTIFICATE OF CORRECTION

PATENT NO. : 11,421,247 B2
APPLICATION NO. : 16/493232
DATED : August 23, 2022
INVENTOR(S) : Keizo Tomonaga et al.

It is certified that error appears in the above-identified patent and that said Letters Patent is hereby corrected as shown below:

In the Specification

In Column 24, Line 8, delete "$1 \times 10^3$" and insert --$1 \times 10^5$--.

In Column 24, Line 10, delete "$1 \times 10^3$" and insert --$1 \times 10^5$--.

In Column 27, Line 59, delete "U.S.A" and insert --U.S.A.--.

In the Claims

In Column 45, Claim 1, Line 22, after "gene", delete "of".

Signed and Sealed this
Eighteenth Day of April, 2023

Katherine Kelly Vidal
*Director of the United States Patent and Trademark Office*